(12) United States Patent
Mitch et al.

(10) Patent No.: US 7,378,448 B2
(45) Date of Patent: May 27, 2008

(54) DIPHENYLETHER AMIDE DERIVATIVES AS OPIOID RECEPTOR ANTAGONISTS

(75) Inventors: Charles Howard Mitch, Columbus, IN (US); Steven James Quimby, Noblesville, IN (US); Miles Goodman Siegel, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/597,127

(22) PCT Filed: Mar. 2, 2005

(86) PCT No.: PCT/US2005/006723

§ 371 (c)(1),
(2), (4) Date: Jul. 12, 2006

(87) PCT Pub. No.: WO2005/092836

PCT Pub. Date: Oct. 6, 2005

(65) Prior Publication Data

US 2007/0066658 A1    Mar. 22, 2007

(51) Int. Cl.
*A61K 31/138* (2006.01)

(52) U.S. Cl. ............ 514/630; 564/220; 564/185; 514/237.5; 514/471; 514/378; 514/448; 514/354; 514/406; 514/620; 514/249; 514/361; 514/357; 544/168; 544/355; 546/323; 546/337; 548/248; 548/374.1; 548/127; 549/487; 549/72

(58) Field of Classification Search ............... 514/613, 514/617, 625, 630
See application file for complete search history.

(56) References Cited

U.S. PATENT DOCUMENTS

| | | | |
|---|---|---|---|
| 2,456,258 | A | 12/1948 | Dohrn et al. |
| 3,976,784 | A | 8/1976 | Coles et al. |
| 5,077,304 | A | 12/1991 | Pascual |
| 5,084,449 | A | 1/1992 | Seydel et al. |
| 5,883,096 | A | 3/1999 | Lowe et al. |

FOREIGN PATENT DOCUMENTS

| | | |
|---|---|---|
| EP | 1 113 000 | 7/2001 |
| EP | 1 193 255 | 4/2002 |
| FR | 2 291 743 | 6/1976 |
| JP | 2001064176 | 3/2001 |
| JP | 2001089412 | 4/2001 |
| WO | WO 99/33806 | 7/1999 |
| WO | WO 00/59878 | 10/2000 |
| WO | WO 02/12224 | 2/2002 |
| WO | WO 02/078693 | 10/2002 |
| WO | WO 03/002519 | 1/2003 |
| WO | WO 2004/026305 | 4/2004 |
| WO | WO 2004/080968 | 9/2004 |
| WO | WO 2004/080996 | 9/2004 |
| WO | WO 2004/093800 | 11/2004 |
| WO | WO 2005/061442 | 7/2005 |
| WO | WO 2005/066164 | 7/2005 |

OTHER PUBLICATIONS

Database Caplus "online," Chemical Abstracts Service, Takahashi, et al, "Pyridine derivatives containing sulfur IV. Snythesis of nitro and aminopyridines," XP002338663.
Database Caplus "online," Chemical Abstracts Service, Acharya, et al., "Synthesis of substituted phenyl 2-pyridyl ethers," XP002338664.
Wenner, et al., "4-Aminomethyl-4'-aminodiphenyl sulfone and related compounds," Journal of Organic Chemistry, vol. 22, pp. 5508-5513 (1957).
Surrey, et al, "Sulfides and sulfones of pyridine and quinoline," Journal of the American Chemical Society, vol. 63, p. 173 (1940).

*Primary Examiner*—Rita Desai
*Assistant Examiner*—David K O'Dell
(74) *Attorney, Agent, or Firm*—John C. Demeter; Francis O. Ginah

(57) ABSTRACT

A compound of the formula (I) wherein the variables $X_1$, $X_2$, B, D, $R^1$ to $R^7$ including $R^{3'}$, p, y, q, and z, are as defined or a pharmaceutically acceptable salt, solvate, enantiomer, racemate, diastereomer or mixtures thereof, useful for the treatment, prevention or amelioration of obesity and Related Diseases is disclosed

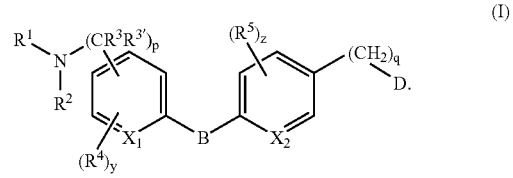

4 Claims, No Drawings

DIPHENYLETHER AMIDE DERIVATIVES AS OPIOID RECEPTOR ANTAGONISTS

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure

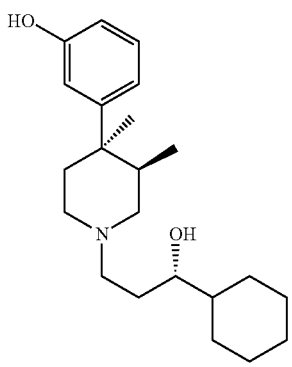

U.S. Pat. No. 6,140,352 discloses the compound of formula Formula 1

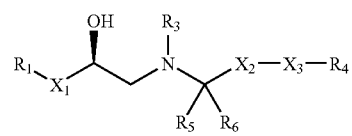

wherein the variables $X_1$, $X_2$, $X_3$ $R_1$, $R_3$, $R_4$, $R_5$ and $R_6$ are as described therein, as agonists of the beta adrenergic receptor useful for the treatment of diabetes and obesity.

PCT application WO 9215304 discloses the compounds of formula I

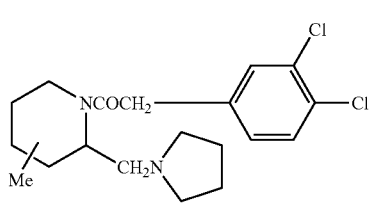

Compound 1 above, encompasses azacyclic and heterocyclic compounds for treatment of cerebral ischemia.

Regardless of these and other disclosures of compounds useful as opioid receptor antagonists, or useful for the treatment of obesity, and/or diabetes by other mechanisms, or having structures partially close to the compounds of the present invention there remains an unmet medical need for useful, safe, effective and/or alternate treatments or prophylaxis of diseases associated with opioid receptors, particularly obesity and Related Diseases.

SUMMARY OF THE INVENTION

The present invention provides a compound of the formula (I)

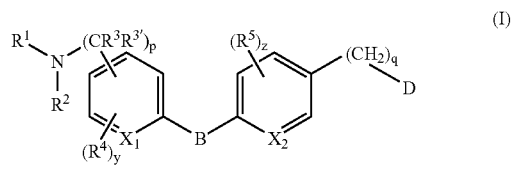

p is 0, 1, or 2;
q is 0, 1, 2, or 3;
y is 0, 1, or 2; and z is 0, 1, or 2;
$X_1$ and $X_2$ are each independently is CH, or N;
B is O, $NR^t$, S, SO, $SO_2$, or $CH_2$;
D is OH, $CONR^6R^7$, $SO_2NR^6R^7$, $NR^6COR^7$, or $NR^6R^7$; provided that when B is O, D is not $CONR^6R^7$;
$R^1$ and $R^2$ are independently selected from hydrogen, $C_1$-$C_8$ alkyl, $C_2$-$C_8$ alkenyl, $C_2$-$C_8$ alkynyl, phenyl, $C_1$-$C_{10}$ alkylaryl, $C_4$-$C_{10}$ alkylcycloalkane, and $(CH_2)_nC(O)R^8$; wherein each of the alkyl, alkenyl, and aryl groups are optionally substituted with one to two groups independently selected from $C_1$-$C_8$ alkyl, $C_2$-$C_8$ alkenyl, phenyl, $C_3$-$C_8$ cycloalkyl, $C_1$-$C_8$ alkylaryl, and $C(O)C_1$-$C_8$ alkyl; and wherein $R^1$ and $R^2$ may optionally combine with each other to form a 4, 5, 6, or 7-membered nitrogen-containing heterocycle which nitrogen-containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_3$ alkylaryl, $C(O)C_1$-$C_8$ alkyl, $CO(O)C_1$-$C_8$ alkyl, halo, $C_1$-$C_3$ haloalkyl;

$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylcycloalkyl, and $C_1$-$C_8$ alkylaryl;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_mNSO_2C_1$-$C_8$ alkyl, $(CH_2)_mNSO_2$phenyl, $(CH_2)_m$NSO$_2$aryl, —$C(O)C_1$-$C_8$ alkyl, and —$C(O)OC_1$-$C_8$ alkyl; wherein each $R^4$ and $R^5$ is attached to its respective ring only at carbon atoms; wherein m is 1 or 2; and n is 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, aryl, $C_1$-$C_8$ alkylaryl, $C_3$-$C_7$ cycloalkane, $C_1$-$C_6$ alkylcycloalkane, $(CH_2)_mC(O)OR^8$, and $(CH_2)_mNSO_2R^8$; wherein each of the alkyl, alkenyl, and aryl groups are optionally substituted with one to two groups independently selected from $C_1$-$C_8$ alkyl, $C_2$-$C_8$ alkenyl, phenyl, and $C_1$-$C_8$ alkylaryl; and wherein when D is $NR^6R^7$ or $SO_2NR^6R^7$, the $R^6$ and $R^7$ groups may independently combine with each other, and with the nitrogen atom to which they are attached to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, and $C_1$-$C_8$ alkylaryl;

$R^t$ is selected from the group consisting of hydrogen, $C_1$-$C_8$ alkyl, $C_2$-$C_8$ alkenyl, $C_2$-$C_8$ alkynyl, phenyl, and $C_1$-$C_8$ alkylaryl;

$R^8$ is independently selected from hydrogen, $C_1$-$C_8$ alkyl, $C_2$-$C_8$ alkenyl, phenyl, benzyl, and $C_5$-$C_8$ alkylaryl;

or a pharmaceutically acceptable salt, solvate, prodrug, enantiomer, racemate, diastereomer, or mixture of diastereomers thereof.

The present invention also provides a method for the prevention, treatment and/or amelioration of the symptoms of obesity and Related Diseases comprising administering a therapeutically effective amount of a compound of formula (I) or a pharmaceutically acceptable salt, solvate, enantiomer, racemate, diastereomer or mixture of diastereomers thereof.

The present invention also provides a pharmaceutical formulation comprising a compound of formula I in association with a carrier, diluent and/or excipient.

The present invention also relates to a method for the treatment and/or prophylaxis of obesity and Related Diseases including eating disorders (bulimia, anorexia nervosa, etc, diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example, gambling, and alcoholism, comprising administering a therapeutically effective amount of a compound of formula I or a pharmaceutically acceptable salt, solvate, enantiomer, racemate, diastereomer or mixture of diastereomers thereof.

The present invention relates to a compound of formula (I) useful for the manufacture of a medicament for the treatment, prevention and/or amelioration of symptoms associated with obesity and Related Diseases.

In another embodiment, the present invention relates to a compound of formula I or a pharmaceutically acceptable salt, solvate, enantiomer, racemate, diastereomer or mixture thereof, useful as an appetite suppressant.

The present invention relates to a method of achieving weight loss while maintaining lean muscle mass or minimizing the loss of lean muscle mass comprising administering a compound of formula I or a pharmaceutically acceptable salt, solvate, enantiomer, racemate, diastereomer or mixture thereof, to a patient in need thereof.

The present invention provides a compound of formula I useful singly or in combination with other agents approved for the treatment, prevention and/or amelioration of obesity and related diseases and symptoms thereof.

DETAILED DESCRIPTION OF THE INVENTION

As used herein, the term "patient" includes human and non-human animals such as companion animals (dogs and cats and the like) and livestock animals.

The preferred patient of treatment, amelioration and/or prevention of obesity and Related Diseases is a human.

The terms "treating" and "treat", as used herein, include their generally accepted meanings e.g. preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of obesity and Related Diseases and the symptoms associated therewith, in a patient afflicted with same or reducing the likelihood that the recipient of a compound of formula I will be afflicted with or develop any of the pathological conditions or sequela thereof described herein.

As used herein, the term "effective amount" is synonymous with "effective dose" and means an amount of a compound of formula I that is sufficient in one or more administrations for preventing, ameliorating or treating a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or a combination of a compounds of formula I or a combination of a compound of formula I and a co-antagonist of the opioid receptor or a combination a compound of formula I and other effective anti-obesity, weight loss or antidiabetic agent.

The term "formulation", as in pharmaceutical formulation, or "pharmaceutical composition" is intended to encompass a product comprising the Active Ingredient (as defined supra), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I and a pharmaceutically acceptable co-antagonist of opioid receptors useful for the treatment and/or prevention of obesity or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression (particularly that induced by the awareness and loss of self esteem associated with obesity), anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia.

As used herein "other agents" approved for the treatment of obesity and/or related disease, or useful for weight loss and/or appetite suppression include but are not limited to Xenical®, Meridia®, Lipitor®, Crestor®, Pravachol®, Zetia®, cannabinoid receptor antagonists, and other opioid receptor antagonists.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a monocycle which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds. A nitrogen containing heterocycle may be attached to or fused to an existing ring substituent thus forming a bicyclic or tricyclic ring system. Nonetheless, the direct result of the formation of a nitrogen containing heterocycle by the joining of two groups and the nitrogen atom to which they are attached is to form a monocycle.

The term "$C_1$-$C_8$ alkyl" or "$C_{1-8}$ alkyl" refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkyaryl means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term "$C_1$-$C_8$ alkylcycloalkyl" refers to a cycloalkane group having a $C_1$-$C_8$ alkyl substituent, and wherein the entire group $C_1$-$C_8$ alkylcycloalkane may itself be a substituent attached at either the alkyl group or the cycloalkyl group to a substrate. The definition and usage applies equally to other homologues of $C_1$-$C_8$ such as for example, $C_1$-$C_7$, $C_1$-$C_6$ etc.

The term "cycloalkane" or "cycloalkyl" means cycloalkanes having from 3 to 8 carbon atoms i.e. from cyclopropane to cyclooctane.

The term "hal" or "halo" as used herein refers to a halogen including fluorine, chlorine, bromine or iodine.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes phenyl, benzyl, naphthyl, but excludes carbazoles and other fused tricyclic ring structures.

It is understood by one of skill in the art that where a substituent is absent, a hydrogen atom is indicated to achieve the required valency unless otherwise indicated. For example, if y is o, then $R^4$ is absent, and all applicable positions on the ring have hydrogen atoms to achieve the required valency for atoms in the ring.

As used herein, the term "protecting group" refers to a groups useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, $3^{rd}$ edition, Greene, T. W.; Wuts, P. G. M. Eds.; John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, maleate, mandelate, mesylate, methylbromide, methylnitrate, methylsulfate, sulfite, sulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

A compound of the invention as illustrated by formula I may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

The compounds of the present invention have shown inhibition of orexigenic effects, and are thus useful as appetite suppressants either as a single therapy or in conjunction with exercise and other effective appetite suppressing or weight loss medications.

PREFERRED EMBODIMENTS OF THE INVENTION

A compound of formula I preferably exists as the free base or a pharmaceutically acceptable salt. More preferred is the hydrochloride salt, the bisulfate salt, mesylate or the oxalic acid salt of the compound of formula I.

For the Groups $R^1$ and $R^2$

Preferred $R^1$ and $R^2$ groups are independently selected from the group consisting of hydrogen, methyl, ethyl, propyl, pentyl, and isopropyl. Also preferred are $R^1$ and $R^2$ groups independently selected from the group consisting of methyl, ethyl, propyl, isopropyl, phenyl,

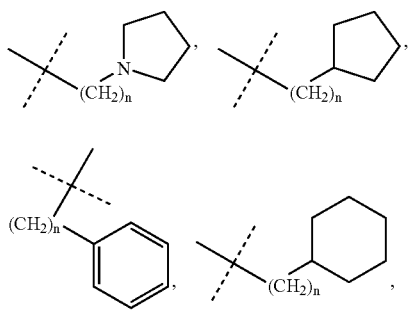

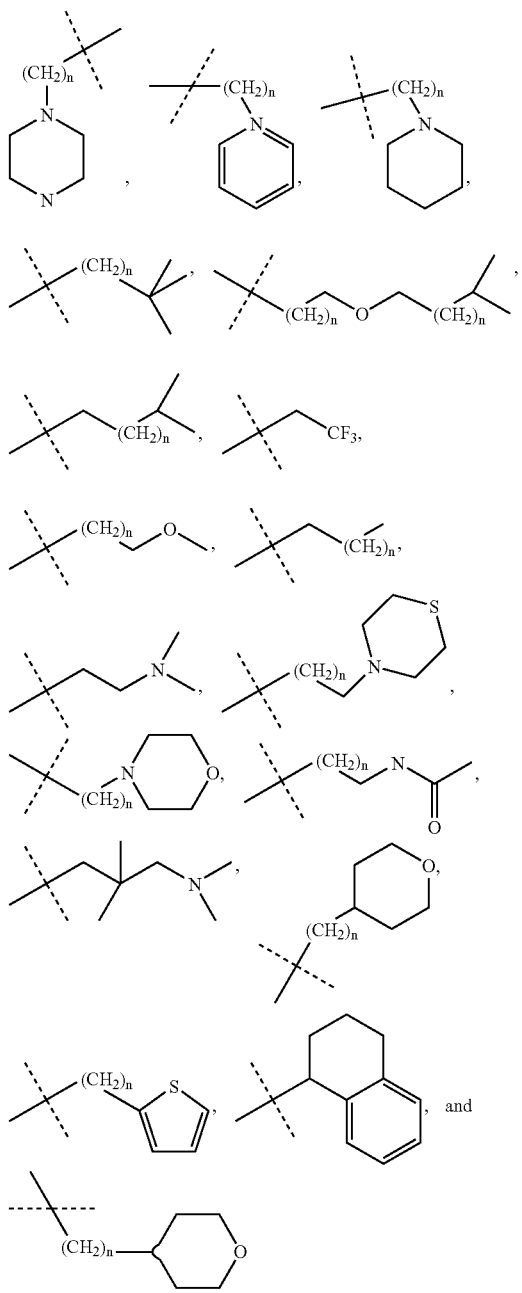

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle.

Also preferred are $R^1$ and $R^2$ groups that combine with each other to form a group selected from the group consisting of each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^3$ and $R^{3'}$ Groups

A preferred $R^3$ is hydrogen. A preferred $R^{3'}$ group is selected from hydrogen, methyl, ethyl, propyl, isopropyl, butyl, isobutyl, phenyl and benzyl. More preferably, both $R^3$ and $R^{3'}$ are hydrogen.

Preferred $R^4$ Groups

A preferred $R^4$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, C1-C5 alkylcycloalkyl, and $C_1$-$C_5$ thioalkyl. More preferred is a $R^4$ group selected from the group consisting of hydrogen, methyl, ethyl, isopropyl, chloro, fluoro, trifluoromethyl, methoxy, ethoxy, thiomethyl, phenyl, and benzyl. Most preferred is an $R^4$ group selected from the group consisting of hydrogen, methyl, ethyl, isopropyl, fluoro, chloro, trifluoromethyl, methoxy, ethoxy, propoxy, isopropoxy, and benzyl.

Though the groups $R^4$ and a $R^5$ may exist as multiple substituents on their respective ring substrates, a preferred embodiment of the invention involves compounds wherein each of $R^4$, and $R^5$ are independently absent, or singly substituted on their respective ring substrates.

Preferred $R^5$ Groups

A preferred $R^5$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, C1-C5 alkylcycloalkyl, and $C_1$-$C_5$ thioalkyl. More preferred is an $R^5$ group selected from the group consisting of hydrogen, methyl, ethyl, isopropyl, chloro, fluoro, trifluoromethyl, methoxy, ethoxy, thiomethyl, phenyl, and benzyl. A most preferred $R^5$ group is selected from the group consisting of hydrogen, methyl, ethyl, isopropyl, fluoro, chloro, trifluoromethyl, methoxy, ethoxy, trifluoromethoxy, and benzyl.

Preferred $R^6$ and $R^7$ Groups

Preferred are $R^6$ and $R^7$ groups independently selected from the group consisting of hydrogen, methyl, ethyl, propyl, pentyl, isopropyl, phenyl and benzyl.

Also preferred are compounds of formula I wherein $R^6$ and $R^7$ independently combine with each other, and with the nitrogen atom to which they are attached to form a 4, 5, 6, or 7-membered nitrogen containing heterocycle which nitrogen containing heterocycle optionally has substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, C(O)$C_1$-$C_8$ alkyl, CO(O)$C_1$-$C_8$ alkyl, hydroxy, $C_1$-$C_8$ alkoxy, halo, and haloalkyl. Most preferred are compounds of the invention wherein $R^6$ and $R^7$ are both hydrogen.

Preferred values for n, m, and p, y, z
A preferred value for n is 0, 1 or 2.
A preferred value for m is 1 or 2.
A preferred value for p is 0, 1, or 2. More preferred is p=1.
A preferred value for y is 0, or 1
A preferred value for z is 0, or 1.
A preferred compound according to the present invention is a compound selected from the group consisting of:
4-[4-(2-Methylamino-ethyl)-phenoxy]-phenol,
4-{4-[2-(Benzyl-methyl-amino)-ethyl]-phenoxy}-phenol,
Acetic acid 4-[4-(2-benzylamino-ethyl)-phenoxy]-phenyl ester,
6-[4-(Benzylamino-methyl)-phenylsulfanyl]-nicotinamide,
6-{4-[(3-Methyl-butylamino)-methyl]-phenylsulfanyl}-nicotinamide,
6-{4-[(2-Pyridin-4-yl-ethylamino)-methyl]-phenylsulfanyl}-nicotinamide,
6-[4-(Phenethylamino-methyl)-phenylsulfanyl]-nicotinamide,
6-{4-[(Cyclopropylmethyl-amino)-methyl]-phenylsulfanyl}-nicotinamide,
6-{4-[(2-Thiophen-2-yl-ethylamino)-methyl]-phenylsulfanyl}-nicotinamide,
6-{4-[(3-Phenyl-propylamino)-methyl]-phenylsulfanyl}-nicotinamide,
6-{4-[(3-Methyl-butylamino)-methyl]-phenylsulfanyl}-nicotinamide,
4-[4-(Phenethyl amino-methyl)-benzenesulfonyl]-benzamide,
4-[4-(Phenethyl amino-methyl)-benzenesulfinyl]-benzamide,
6-[4-(2-Benzylamino-ethyl)-phenylamino]-nicotinamide,
6-{4-[2-(Cyclohexylmethyl-amino)-ethyl]-phenylamino}-nicotinamide,
6-{4-[(2-Pyridin-4-yl-ethylamino)-methyl]-phenylsulfanyl}-nicotinamide,
6-[4-(Benzylamino-methyl)-phenylamino]-nicotinamide,
6-{4-[(Cyclohexylmethyl-amino)-methyl]-phenylamino}-nicotinamide,
6-[4-(Phenethylamino-methyl)-phenylamino]-nicotinamide,
6-{4-[(3-Methyl-butylamino)-methyl]-phenylamino}-nicotinamide,
N-{4-[4-(2-Benzylamino-ethyl)-phenoxy]-phenyl}-acetamide,
N-{4-[4-(2-Hexylamino-ethyl)-phenoxy]-phenyl}-acetamide,
N-[4-(4-{2-[(Thiophen-2-ylmethyl)-amino]-ethyl}-phenoxy)-phenyl]-acetamide,
N-(4-{4-[2-(3-Phenyl-propylamino)-ethyl]-phenoxy}-phenyl)-acetamide,
N-(4-{4-[2-(2-Cyclohexyl-ethylamino)-ethyl]-phenoxy}-phenyl)-acetamide,
N-{4-[4-(2-Phenethylamino-ethyl)-phenoxy]-phenyl}-acetamide,
N-{4-[4-(2-Propylamino-ethyl)-phenoxy]-phenyl}-acetamide,
N-{4-[4-(2-Pentylamino-ethyl)-phenoxy]-phenyl}-acetamide, N-(4-{4-[2-(Cyclohexylmethyl-amino)-ethyl]-phenoxy}-phenyl)-acetamide,
N-(4-{4-[2-(2-Trifluoromethyl-benzylamino)-ethyl]-phenoxy}-phenyl)-acetamide,
N-[4-(4-{2-[(Furan-2-ylmethyl)-amino]-ethyl}-phenoxy)-phenyl]-acetamide,
N-(4-{4-[2-(3-Chloro-benzylamino)-ethyl]-phenoxy}-phenyl)-acetamide,
4-[4-(2-Benzylamino-ethyl)-phenoxy]-phenylamine,
N-{4-[4-(2-Benzylamino-ethyl)-phenoxy]-phenyl}-benzamide,
Morpholine-4-carboxylic acid {4-[4-(2-benzylamino-ethyl)-phenoxy]-phenyl}-amide,
N-{4-[4-(2-Benzylamino-ethyl)-phenoxy]-phenyl}-2-methoxy-acetamide,
Furan-2-carboxylic acid {4-[4-(2-benzylamino-ethyl)-phenoxy]-phenyl}-amide,
Isoxazole-5-carboxylic acid {4-[4-(2-benzylamino-ethyl)-phenoxy]-phenyl}-amide,
Thiophene-2-carboxylic acid {4-[4-(2-benzylamino-ethyl)-phenoxy]-phenyl}-amide,
N-{4-[4-(2-Benzylamino-ethyl)-phenoxy]-phenyl}-isonicotinamide,
3,5-Dimethyl-isoxazole-4-carboxylic acid {4-[4-(2-benzylamino-ethyl)-phenoxy]-phenyl}-amide,
2-tert-Butyl-5-methyl-2H-pyrazole-3-carboxylic acid {4-[4-(2-benzylamino-ethyl)-phenoxy]-phenyl}-amide,
5-Methyl-isoxazole-3-carboxylic acid {4-[4-(2-benzylamino-ethyl)-phenoxy]-phenyl}-amide,
4-Methyl-[1,2,3]thiadiazole-5-carboxylic acid {4-[4-(2-benzylamino-ethyl)-phenoxy]-phenyl}-amide,
N-{4-[4-(2-Benzylamino-ethyl)-phenoxy]-phenyl}-3-methylsulfanyl-propionamide,
Quinoxaline-2-carboxylic acid {4-[4-(2-benzylamino-ethyl)-phenoxy]-phenyl}-amide,
N-{4-[4-(2-Benzylamino-ethyl)-phenoxy]-phenyl}-nicotinamide,
Pyridine-2-carboxylic acid {4-[4-(2-benzylamino-ethyl)-phenoxy]-phenyl}-amide,
N-(6-{4-[(3-Methyl-butylamino)-methyl]-phenoxy}-pyridin-3-yl)-acetamide, or a pharmaceutically acceptable salt, solvate, enantiomer, diastereomer and diastereomeric mixture thereof.

Preparing Compounds of the Invention

Compounds of formula I may be prepared as described in the following schemes and/or examples or following a combination of schemes know to one of skill in the art for making fragments and combinations thereof. Compounds employed as initial starting materials in the synthesis of compounds of the invention are well known and, to the extent not commercially available, are readily synthesized using specific references provided, or by standard procedures commonly employed by those of ordinary skill in the art and/or found in general reference texts.

More particularly, the compounds of the invention are produced in accordance with schemes 1 through 3 that are described in detail below, or analogous methods thereto. These reactions are often carried out following known procedures, methods, or analogous methods thereto. Examples of such known procedures and/or methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Compounds of the invention may be prepared following the procedures discussed in the scheme s below, the experimental section or following known variations of same. Scheme I for example shown the preparation of compounds of formula I wherein B is O, and D is other than CONR$^6$R$^7$.

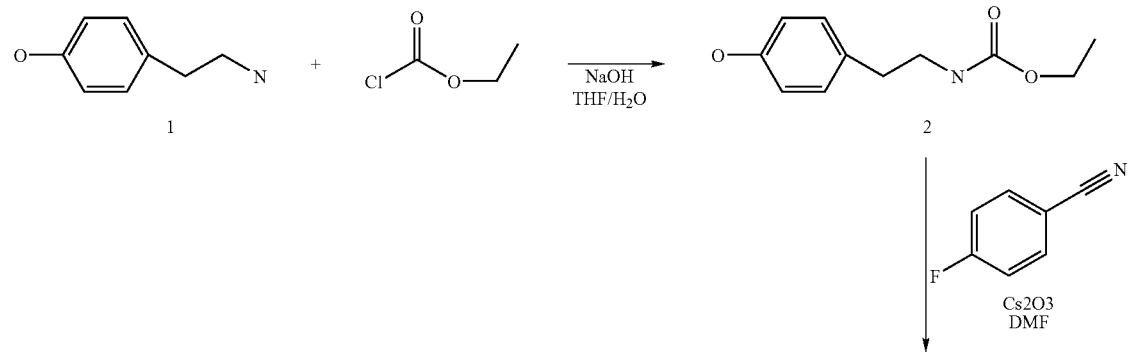

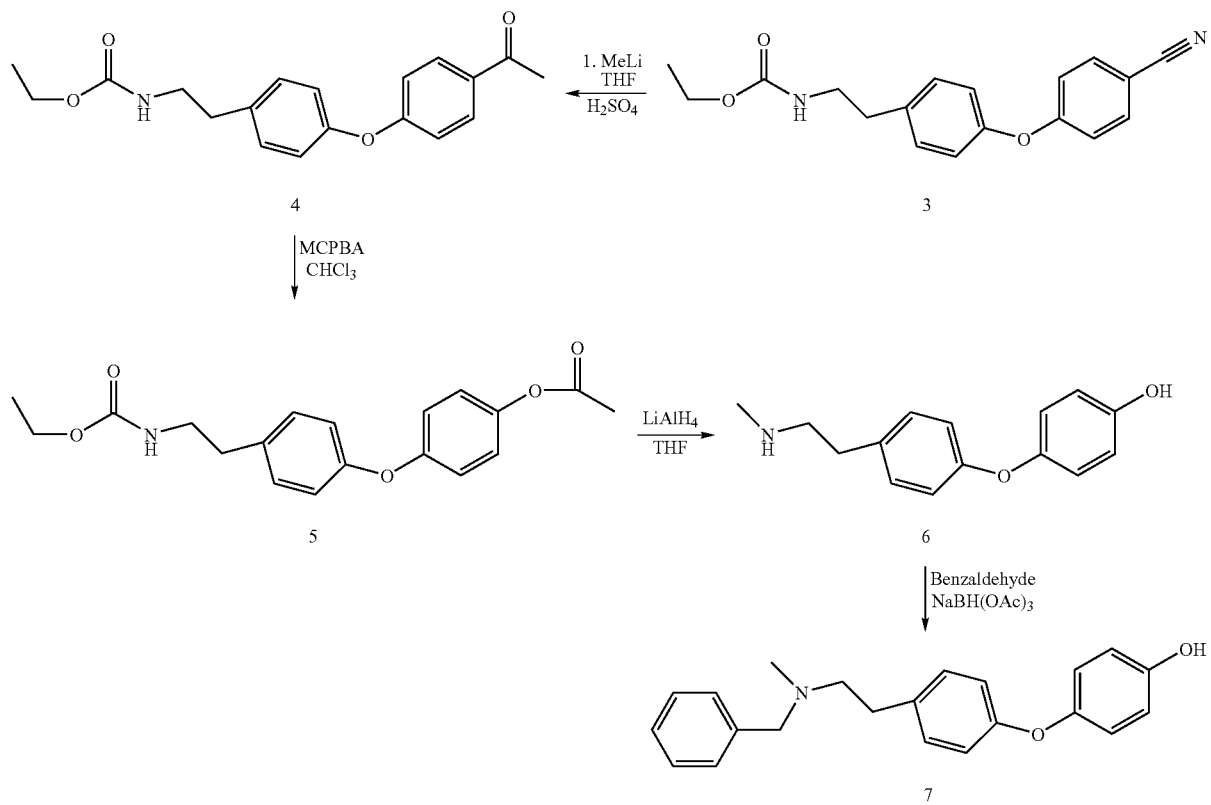

According to scheme 1, ethyl chloroformate is added to a solution of tyramine (1), sodium hydroxide, and water to produce the [2-(4-hydroxy-phenyl)-ethyl]-carbamic acid ethyl ester (2). The carbamate is treated with cesium carbonate and 4-fluorobenzonitrile in DMF to yield the corresponding biarylether 3. The nitrile functionality of the biaryl; ether 3 is converted to the N-acyl compound 4 by reaction with mrethyllithium followed by hydrolysis in aqueous sulfuric acid. The N-acyl compound 4 is converted to the acetate 5 by oxidation with m-chloroperbenzoic acid (MCPBA) in a suitable solvent. The acetate 5 is reduced with lithium aluminum hydride to afford the compound 4-[4-(2-methylamino-ethyl)-phenoxy]-phenol (6). The compound 6 is treated with benzaldehyde in the presence of sodium triacetoxyborohydride to produce the reductive amination product 4-{4-[2-(benzyl-methyl-amino)-ethyl]-phenoxy}-phenol 7 of formula I. Compounds of formula I wherein D is acetate and q is 0, may also be prepared according to scheme 2 below.

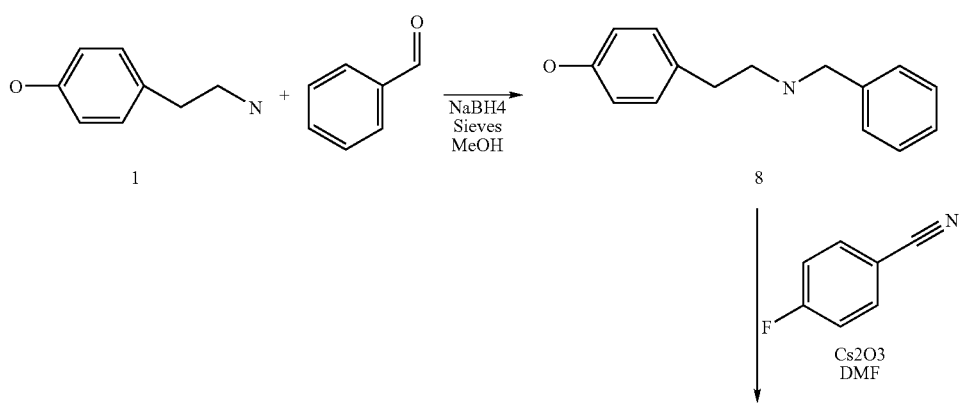

-continued

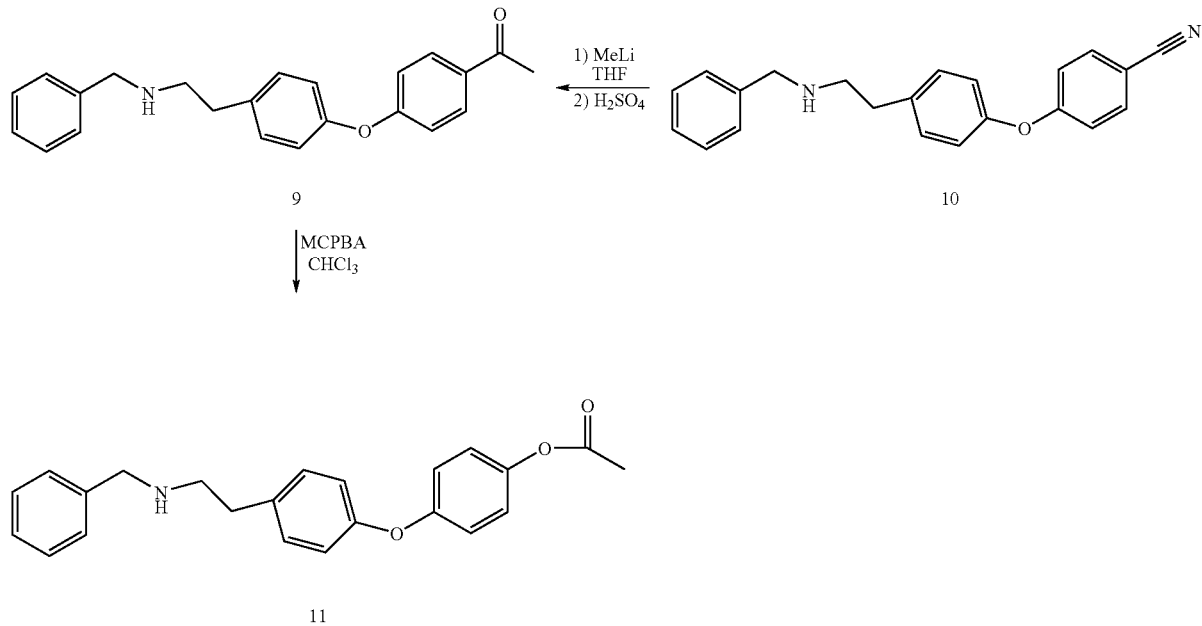

Accordiong to Scheme 2, tyramine is treated with benzaldehyde in sodium borohydride, molecular sieves, and methanol to produce the reductive amination product 4-(benzylamino-ethyl)-phenol (8). The phenol 8 is treated with cesium carbonate and 4-fluorobenzonitrile in DMF to yield the corresponding biarylether 9. The nitrile functionality of the biaryl ether may be converted to the actetate 10 with methyl lithium followed by hydrolyis in aqueous sulfuric acid. The acetate 10 is oxidized with MCPBA to yield acetic acid 4-[4-(2-benzylamino-ethyl)-phenoxy]-phenyl ester (11).

Compounds of the invention wherein B is S, SO or $SO_2$ may be prepared following the procedure of scheme 3 and/or modifications thereof.

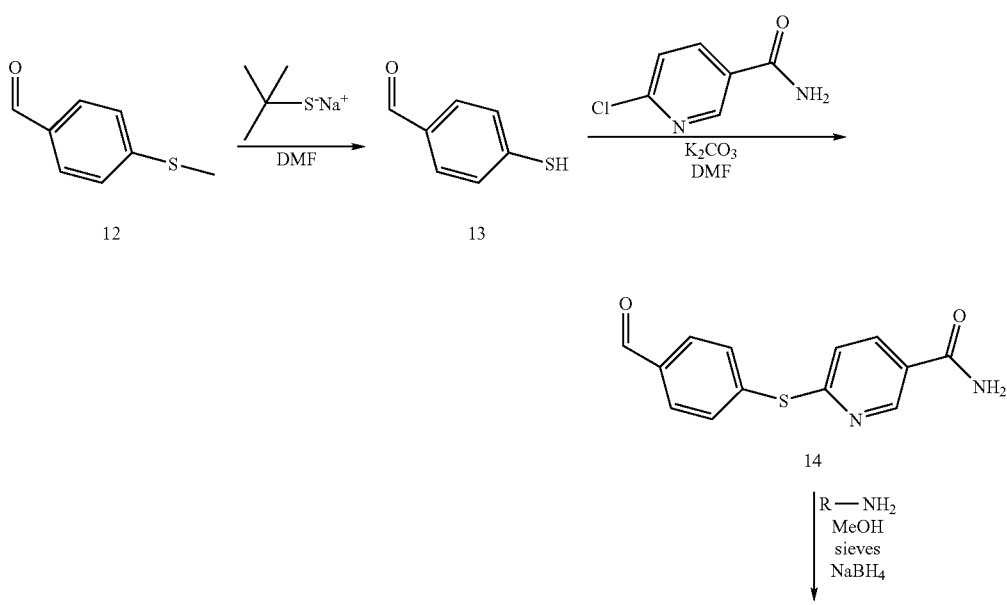

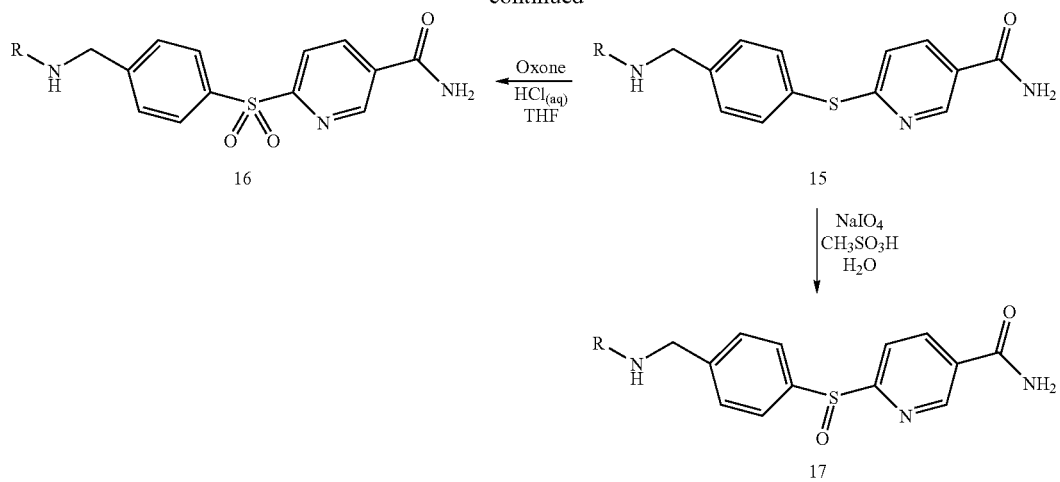

According to scheme 3, 4-(Methylthio)benzaldehyde (12) or analog thereof, is demethylated with 2-methyl-2-propanethiol sodium salt to yield the 4-mercapto-benzaldehyde 13. The thiol product 13 is treated with potassium carbonate and 6-chloro-nicotinamide or other halonicotinamide or halobanzamide in DMF to afford the corresponding biarylthioether 14. Reductive amination of the biarylthiother 14 with a desired amine in the presence of sodium borohydride, molecular sieves, and methanol affords upon workup and isolation the carboxamide compound 15. Oxidative conditions were employed to produce the corresponding sufoxide and sulfone. For example, ozonlolysis of compound 15 affords the sulfone 16, while oxidation using sodium periodate affords the sulfoxide 17, both compounds of formula I.

Compounds of the invention wherein B is NH may be prepared following the protocol of Scheme 4.

tinamide (19). The nitrile 19 is catalytically reduced using procedures known to one of skill in the art such as for example, 5-10% palladium on carbon with or without other co-catalysts to afford the primary amine (20). Alternatively, an amino nicotinonitrile may be reacted with an appropriately substituted halobenzamide or halonicotinamide to afford the corresponding coupled nitrile product (analog of 20). The coupled nitrile product 19 or analog thereof is then reduced as discussed above to afford the corresponding primary amine 20 or analog thereof. The primary amine 20 is treated with the appropriate aldehyde under reductive amination conditions using sodium borohydride, molecular sieves, and methanol, to produce the desired compound of formula I, e.g. compound 21.

Scheme 4

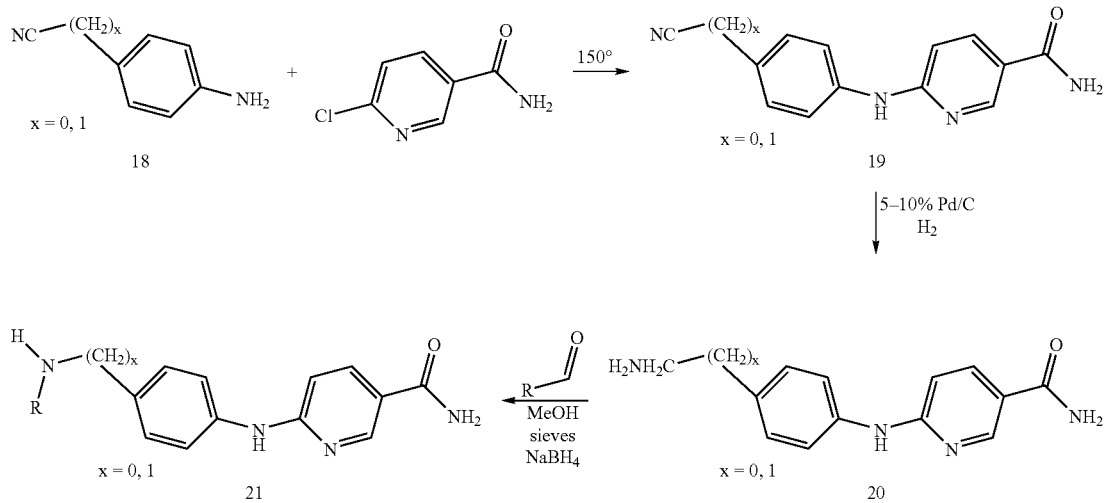

As shown in Scheme 4, the desired aminonitrile e.g. 4-amino benzonitrile (18) is combined with 6-chloro-nicotinamide at about 150° C. to produce the phenylaminonico- Compounds of formula I where D is a reverse amide ($NR^6COR^7$) may be prepared following the protocol of Scheme 5.

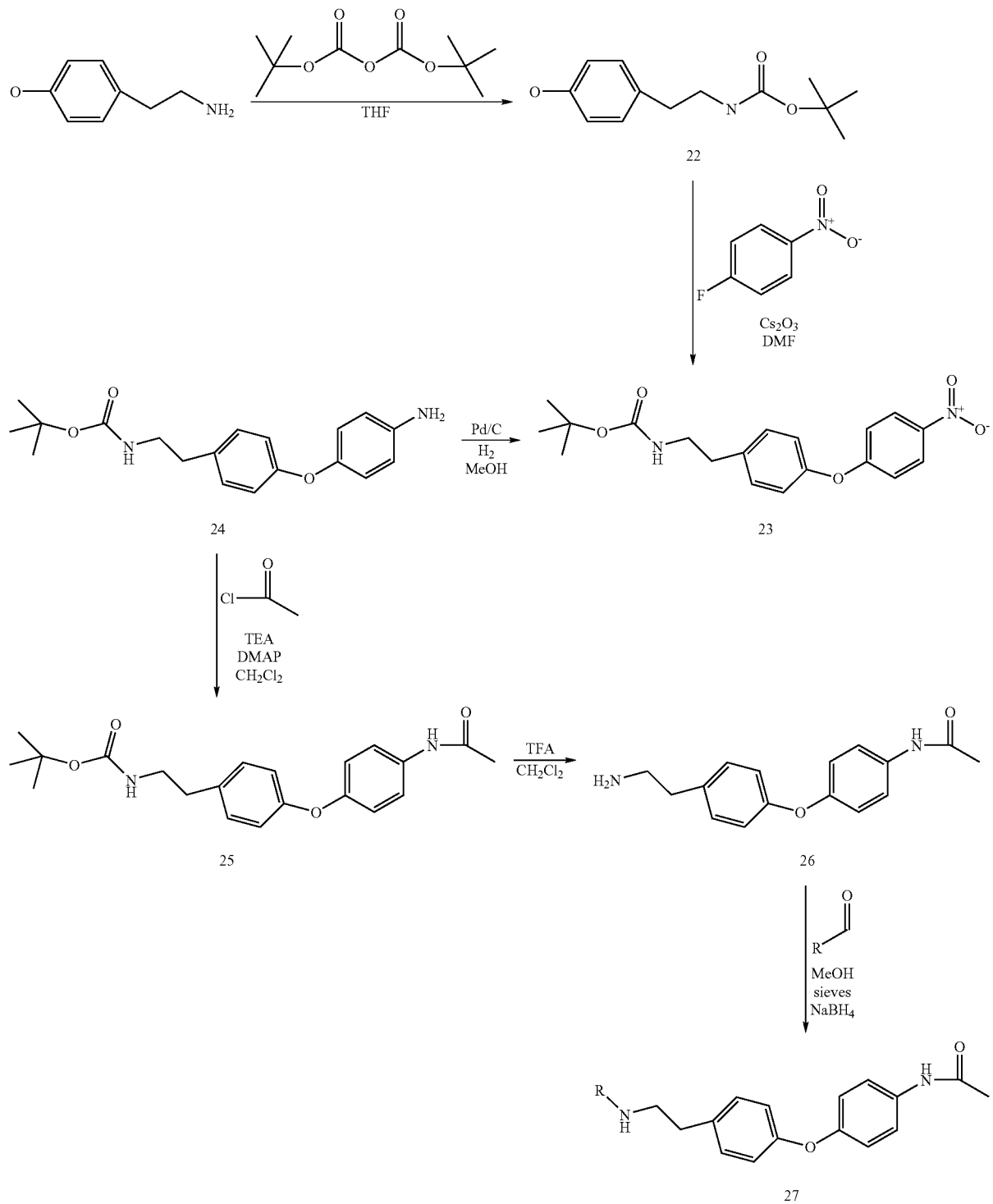

Scheme 5

As shown in scheme 5, tyramine is protected as the t-butyl carbamate 22 and then reacted with 4-fluoronitrobenzene with cesium carbonate in DMF to yield the corresponding biarylether, {2-[4-(4-nitro-phenoxy)-phenyl]-ethyl}-carbamic acid tert-butyl ester (19). Compound 19 is reduced by catalytic hydrogenation with palladium on carbon at the nitro group to afford the amine 23. Compound 23 is then N-acylated with acetyl chloride to afford the N-acyl compound 25. The t-Boc protecting group is removed from compound 25 using TFA in dichloromethane and the resulting amine 26 is reacted with various aldehydes under reductive amination conditions to afford compound 27.

Compounds of formula I wherein D is a reverse amide may also be prepared following the protocol of scheme 6
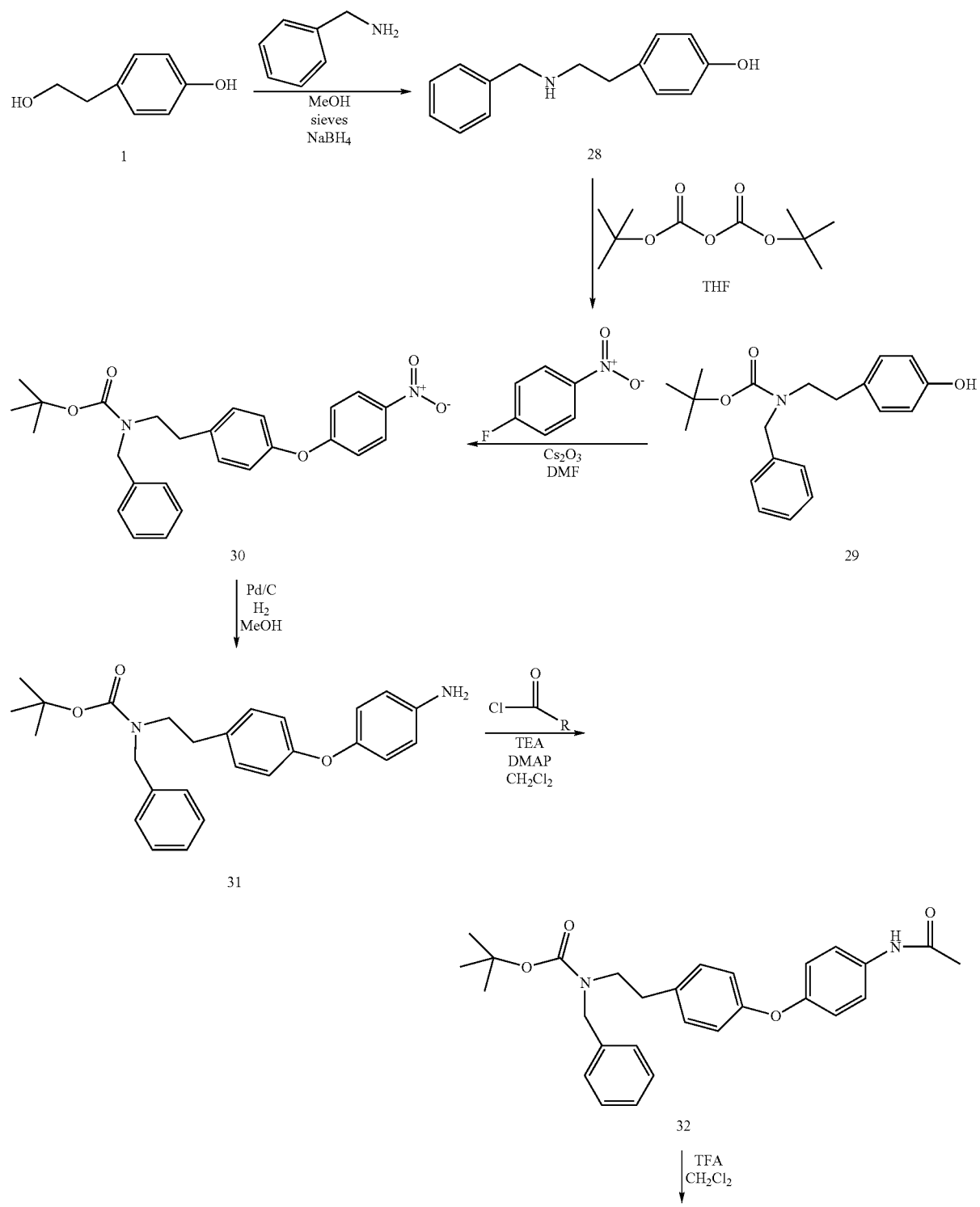

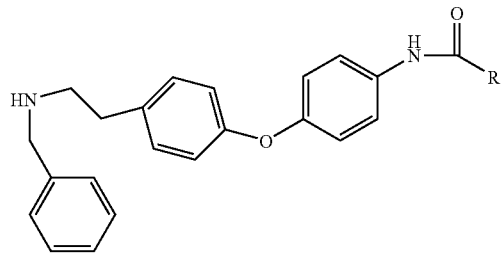

33

According to scheme 6, tyramine (1) is reacted with benzaldehyde under reductive amination conditions to yield 4-(2-benzylamino-ethyl)-phenol (28). The amine 28 is protected as the t-butyl carbamate (29). The carbamate 29 is reacted with 4-fluoronitrobenzene under basic reaction conditions (as shown or known modifications thereof) to afford the coupled product 30. The coupled product 30 is then reduced at the nitro group utilizing catalytic hydrogenation (palladium on carbon) to afford {2-[4-(4-amino-phenoxy)-phenyl]-ethyl}-benzyl-carbamic acid tert-butyl ester (31). The resulting amine 31 may be acylated with one of various acid chlorides to form the desired reverse amide compound 32. The Boc protecting group is removed with TFA in dichloromethane to afford compound 33, a compound of the invention.

sodium triacetoxyborohydride, acectic acid, and dichloromethane to yield the reductive amination product [4-(5-bromo-pyridin-2-yloxy)-benzyl]-(3-methyl-butyl)-amine (36). The resulting aryl bromide 36 is treated with acetamide, copper iodide, and 1,2 diaminocyclohexane in dioxane to yield the target compound 37.

Though protocols have been provided above for the preparation of specific examples one of skill in the art is aware that other compounds of formula I or analogs of those thought in the protocols ma be prepared following generally the protocols disclosed. For example, optionally substituted analogs and isomers of may be prepared using the appropriate analogs of starting materials including positional isomers and optionally substituted analogs of starting materials, and intermediates. Similarly, one of skill is aware of

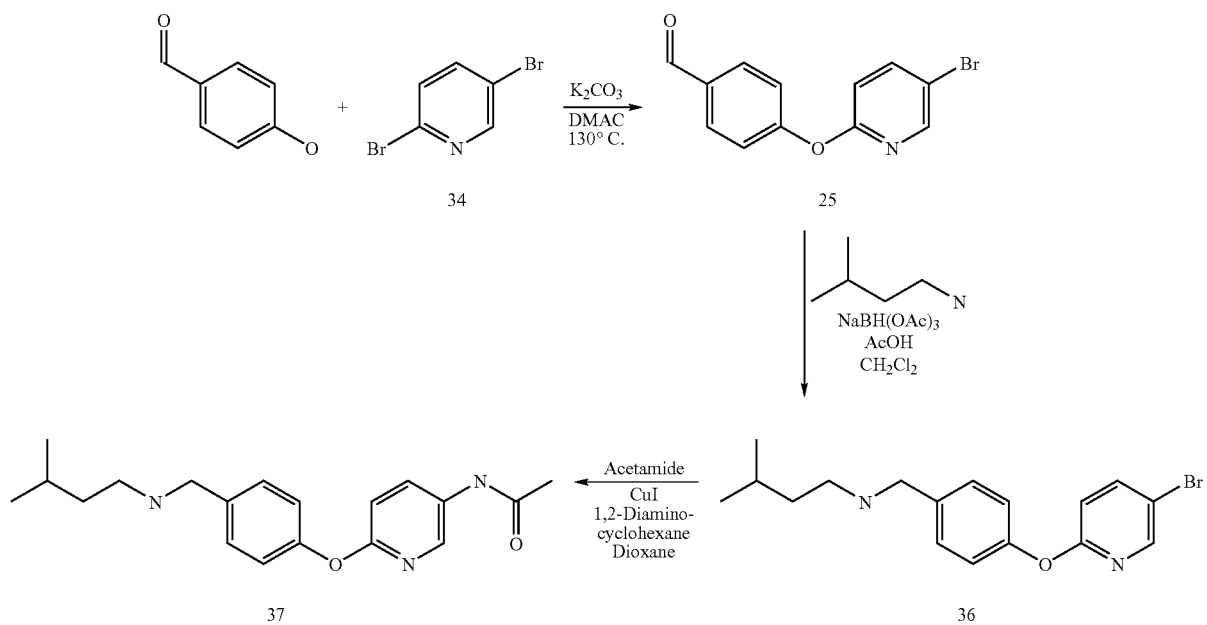

As shown in scheme 7, 4-Hydroxybenzaldehyde is treated with potassium carbonate and 2,5-dibromopyridine in DMAC to afford 4-(5-bromo-pyridin-2-yloxy)-benzaldehyde (35). The aldehyde 35 is combined with isoamylamine, suitable solvents, temperatures and other routine reaction conditions in addition to or in place of those disclosed that may be necessary to effect improved yields for particular substrates or target products.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I.

The term "receptor blocking dose", as used herein, means an amount of a compound of formula I necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof.

Assay Methodology

The compounds of the present invention have been found to display useful activity in an opioid receptor binding assay which measures the ability of the compounds to block the mu, kappa, delta or receptor combination (heterodimer) thereof.

The functional antagonist potency (Kb) of the sample compounds was determined using the GTPγS binding assay. GTPgS—based functional assays provide an in vitro measure of the activity of opioid agonists and antagonists. Opioid reference compounds or test compound are incubated with membrane homogenate from cells expressing the cloned human mu, kappa or delta opioid receptor and radiolabeled [35S]GTPgS. If the compound activates the opioid receptor, an increase in the binding of radiolabeled GTPgS is observed. Similarly, if the compound exhibits antagonist activity, it interferes with the ability of the control agonist to stimulate GTPgS binding. These tests provide an in vitro measurement of the activity of the compound at human opioid receptors.

GTP-γ-S Binding Assay

An SPA-based GTP-γ-S assay format was developed based on previous opioid (Emmerson et al., J. Pharm Exp Ther 278,1121,1996; Horng et al., Society for Neuroscience Abstracts, 434.6, 2000) and muscarinic (DeLapp et al., JPET 289, 946, 1999) assay formats. Membranes were resuspended in 20 mM HEPES, 100 mM NaCl, 5 mM $MgCl_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For anatagonist assays, specific agonists were added at the following concentrations: (MOR) DAMGO 1 micromolar, (DOR) DPDPE 30 nM, (KOR) U69593 300 nm. Kb's were determined by Cheng-Prusoff equation (see Cheng and Prusoff, Biochem. Pharmacol. 22, 3099, 1973). Results obtained for a sample of compounds of the invention in the GTP-γ-S Binding Assay are shown in table 1 below.

TABLE 1

| Example # | Receptor Binding (Ki, nM) | | |
|---|---|---|---|
| | Mu | Kappa | Delta |
| 24 | 197.995 | 2666.625 | 4024.180 |
| 25 | 67.475 | 3971.810 | 2513.985 |
| 27 | 64.255 | 618.350 | 1319.600 |
| 28 | 26.905 | 149.815 | 469.235 |
| 29 | 5.055 | 731.050 | 62.535 |
| 27 | 199.880 | >5000 | >5000 |
| 30 | 18.015 | 163.050 | 260.150 |
| 10 | 726.185 | >5000 | 3036.670 |
| 6 | 228.725 | 1616.740 | 3249.040 |
| 5 | 1314.740 | >5000 | >5000 |
| 36 | >2500 | >4000 | >5000 |
| 37 | 1753.830 | >4000 | >5000 |
| 38 | 1721.810 | >4000 | >5000 |
| 39 | >2500 | >4000 | >5000 |
| 40 | 911.870 | >4000 | >5000 |
| 13 | 563.465 | 2435.285 | 3523.735 |
| 14 | 86.445 | 1022.330 | 714.465 |
| 15 | 292.470 | 653.775 | 1824.015 |
| 16 | 45.395 | 1018.085 | 269.740 |
| 17 | 1347.320 | 761.245 | >5000 |
| 18 | 48.740 | 466.448 | 278.380 |
| 19 | 107.185 | 137.380 | 858.035 |
| 20 | 73.240 | 402.045 | 537.255 |
| 21 | >3000 | >4000 | >5000 |
| 22 | >3000 | >4000 | >5000 |

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient therefore.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders, which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
|---|---|---|
| Active Ingredient | 250 | 38 |
| Cellulose microcrystalline | 400 | 60 |

| Compound | Amount per capsule (mg) | Percent by weight (%) |
|---|---|---|
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
|---|---|
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
|---|---|
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLES

Compounds of the invention may be prepared following procedures disclosed herein or known modifications thereof. Unless otherwise indicated, reagents are generally available from chemical distributors including those specializing in fine limited use chemicals.

Example 1

Step 1

[2-(4-Hydroxy-phenyl)-ethyl]-carbamic acid ethyl ester

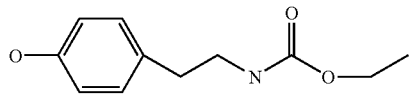

Add dropwise via an addition funnel a solution of ethyl chloroformate (0.74 mL, 7.7 mmol) in tetrahydrofuran (7 mL) to a stirred solution of tyramine (1.0 g, 7.3 mmol), sodium hydroxide (0.7 g, 17.1 mmol), and water (7 mL). Stir at room temperature for 18 hours then pour the reaction into 1N aqueous hydrochloric acid so the pH=1-2. Extract with ethyl acetate (3×25 mL). Dry the combined ethyl acetate extracts over sodium chloride/magnesium sulfate, filter, and concentrate on a rotary evaporator to yield 1.3 g, 6.2 mmol of [2-(4-hydroxy-phenyl)-ethyl]-carbamic acid ethyl ester: $^1$H NMR (CDCl3, 300.00 MHz): 7.01 (d, 2H); 6.78 (d, 2H); 6.26 (s, 1H); 4.78 (s, 1H); 4.14-4.09 (m, 2H); 3.40-3.38 (m, 2H); 2.74-2.69 (m, 2H); 1.24-1.19 (m, 3H).

Step 2

{2-[4-(4-Cyano-phenoxy)-phenyl]-ethyl}-carbamic acid ethyl ester

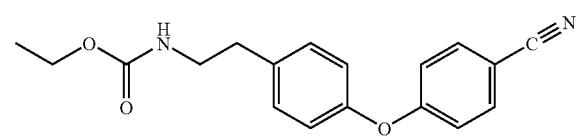

Combine 6.2 mmol of [2-(4-hydroxy-phenyl)-ethyl]-carbamic acid ethyl ester (3.6.0 g, 17.2 mmol), 4-fluorobenzonitrile (2.1 g, 17.2 mmol), cesium carbonate (11.2 g, 34.4 mmol), and N,N-dimethylformamide (80 mL), stir and heat at 85° C. for 18 hours. Cool to room temperature and evaporate on a rotary evaporator, took up residue in brine then extracted with ethyl acetate (3×50 mL). Dry the combined ethyl acetate extracts over sodium chloride/magnesium sulfate, filter, and concentrate on a rotary evaporator to yield the crude product (4.5 g). The crude product is purified by flash column chromatography on silica gel eluting with ethyl acetate and hexanes to yield {2-[4-(4-cyano-phenoxy)-phenyl]-ethyl}-carbamic acid ethyl ester (2.3 g): $^1$H NMR (CDCl3, 300.00 MHz): 7.66-7.60 (m, 2H), 7.31-7.24 (m, 2H), 7.07-7.00 (m, 4H), 4.72 (s, 1H), 4.16 (q, 2H, J=7.0 Hz), 3.48 (q, 2H, J=6.7 Hz), 2.86 (t, 2H, J=7.0 Hz), 1.27 (t, 3H, J=7.0 Hz).

Step 3

{2-[4-(4-Acetyl-phenoxy)-phenyl]-ethyl}-carbamic acid ethyl ester

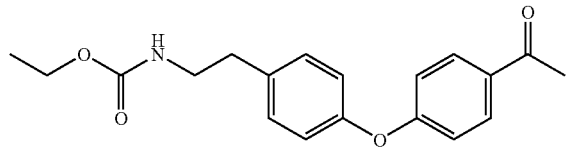

1.4M methyl lithium in diethyl ether (23.2 mL, 32.5 mmol) was added via syringe to a solution of {2-[4-(4-cyano-phenoxy)-phenyl]-ethyl}-carbamic acid ethyl ester (2.0 g, 6.5 mmol) in tetrahydrofuran (50 mL) while stirring at −78° C. for 4 hours. Added 3M aqueous sulfuric acid (10.8 mL, 32.5 mmol) to the reaction via a syringe then warm to room temperature for 2 hours. The reaction was allowed to stand for 72 hours, quenched with saturated aqueous sodium bicarbonate then extracted with dichloromethane (3×75 mL). The combined dichloromethane extracts were dried over sodium chloride/magnesium sulfate, filtered, and concentrated on a rotary evaporator to yield the crude product (2.1 g). The crude product is purified by flash column chromatography on silica gel eluting with ethyl acetate and hexanes to yield {2-[4-(4-acetyl-phenoxy)-phenyl]-ethyl}-carbamic acid ethyl ester (2.0 g): $^1$H NMR (CDCl3, 300.00 MHz): 8.0-7.9 (m, 2H), 7.25-7.15 (m, 2H), 7.05-6.95 (m, 4H), 4.75 (s, 1H), 4.15 (q, 2H), 3.45 (q, 2H), 2.85 (t, 2H), 2.55 (s, 3H), 1.25 (t, 3H).

Example 2

Acetic acid 4-[4-(2-ethoxycarbonylamino-ethyl)-phenoxy]-phenyl ester

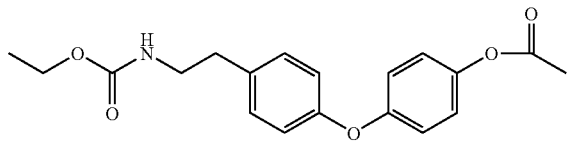

Metachloroperbenzoic Acid (1.2 g, 4.1 mmol) was added to a solution of {2-[4-(4-acetyl-phenoxy)-phenyl]-ethyl}-carbamic acid ethyl ester (1.0 g, 3.1 mmol) in chloroform (75 mL). Stirred at room temperature for 72 hours, quenched with saturated aqueous Na$_2$S$_2$O$_3$, then extracted with dichloromethane (3×75 mL). The combined dichloromethane extracts were dried over sodium chloride/magnesium sulfate, filtered, and concentrated on a rotary evaporator to yield the crude product (2 g). The crude product was purified by flash column chromatography on silica gel eluting with ethyl acetate and hexanes to yield Acetic acid 4-[4-(2-ethoxycarbonylamino-ethyl)-phenoxy]-phenyl ester (430 mg). $^1$H NMR (CDCl3, 300.00 MHz): 7.19-6.92 (m, 8H), 4.98 (s, 1H), 4.17-4.07 (m, 2H), 3.42 (q, 2H, J=6.6 Hz), 2.79 (t, 2H, J=7.2 Hz), 2.29 (s, 3H), 1.30-1.20 (m, 3H), 1.30-1.20 (m, 3H), 1.30-1.20 (m, 3H).

Example 3

Step 1

4-[4-(2-Methylamino-ethyl)-phenoxy]-phenol

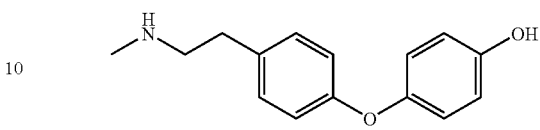

1.0M Lithium aluminum hydride in tetrahydrofuran (5 mL) was added to a solution of acetic acid 4-[4-(2-ethoxycarbonylamino-ethyl)-phenoxy]-phenyl ester (330 mg, 1.0 mmol) in tetrahydrofuran (25 mL). Refluxed overnight, cooled to room temperature, then quenched the reaction with saturated aqueous ammonium chloride and stirred for 3 hours. Decanted the organic layer. Washed the remaining solid with ethyl acetate (2×30 mL). Combined all the organic washes then concentrated on a rotary evaporator to yield 4-[4-(2-Methylamino-ethyl)-phenoxy]-phenol (200 mg): HPLC=98% (5/95 to 95/5 ACN/(0.1% TFA in water) over 10 minutes, Zorbax SB-Phenyl 4.6 mm×15 cm×5 micron, λ=254 nM. $^1$H NMR (CDCl3, 300.00 MHz): 7.42-6.77 (m, 8H), 4.32 (s, 1H), 2.95-2.79 (m, 4H), 2.52 (s, 3H).

Step 2

4-{4-[2-(Benzyl-methyl-amino)-ethyl]-phenoxy}-phenol

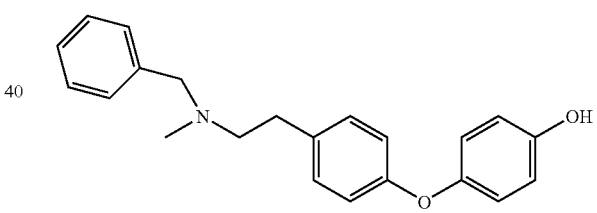

Sodium triacetoxyborohydride (131 mg, 0.62 mmol) was added to a solution of 4-[4-(2-Methylamino-ethyl)-phenoxy]-phenol (75 mg, 0.31 mmol), benzaldehyde (34 mg, 0.32 mmol), acetic acid (19 mg, 0.32 mmol), and 1,2-dichloroethane (5 mL). Stirred the reaction at room temperature overnight, quenched with a pH=10 buffer, then extracted with dichloromethane (3×25 mL). The combined dichloromethane extracts were dried over sodium chloride/magnesium sulfate, filtered, and concentrated on a rotary evaporator to yield the crude product (100 mg). The crude product is purified by flash column chromatography on silica gel eluting with ethanol in dichloromethane to yield 4-{4-[2-(benzyl-methyl-amino)-ethyl]-phenoxy}-phenol, (60 mg): m/z=334.01(M+1); HPLC=97% (5/95 to 95/5 ACN/(0.1% TFA in water) over 10 minutes, Zorbax SB-Phenyl 4.6 mm×15 cm×5 micron, λ=254 nM. $^1$H NMR (CDCl3, 300.00 MHz): 7.42-7.28 (m, 7H), 7.11-7.05 (m, 2H), 6.97-6.79 (m, 4H), 3.63 (s, 2H), 2.86-2.78 (m, 2H), 2.71-2.63 (m, 2H), 2.33 (s, 3H),

Example 4

Step 1

4-(2-Benzylamino-ethyl)-phenol

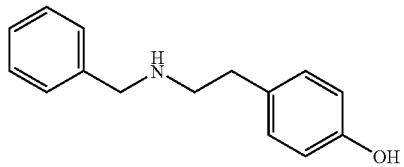

Combine tyramine (5 g, 36.5 mmol), benzaldehyde (9.9 g, 45.6 mmol), 3 Å molecular sieves (10 g), and methanol (200 mL) and stir overnight at room temperature. Cool to 5° C. then add sodium borohydride (5.5 g, 146 mmol) to the reaction. Stir for 2 hours then concentrate on a rotary evaporator. Dilute in methanol, filter, then concentrate on a rotary evaporator. The residue was taken up in 1N hydrochloric acid and washed with diethyl ether. The aqueous layer was basified then extracted with ethyl acetate (2×100 mL). The ethyl acetate extracts were combined, dried over sodium chloride/magnesium sulfate, filtered, and concentrated on a rotary evaporator to yield 4-(2-Benzylamino-ethyl)-phenol (3.3 g) $^1$H NMR(CDCl3, 300.00 MHz): 9.14 (s, 1H), 7.35-7.20 (m, 5H), 7.01-6.96 (m, 2H), 6.69-6.64 (m, 2H), 5.19 (s, 1H), 3.73 (s, 2H), 2.72-2.60 (m, 4H).

Step 2

4-[4-(2-Benzylamino-ethyl)-phenoxy]-benzonitrile

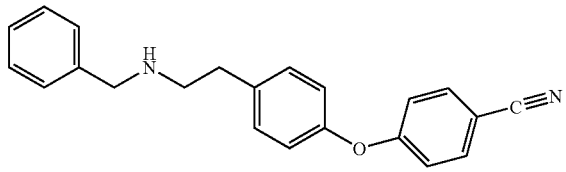

Reaction of 4-fluorobenzonitrile with the compound of Example 4, step 1 following the procedure of Example 1, step 2. affords the title compound, 4-[4-(2-Benzylamino-ethyl)-phenoxy]-benzonitrile, (2.7 g): $^1$H NMR (CDCl3, 300.00 MHz): 7.65-7.58 (m, 2H), 7.41-7.25 (m, 7H), 7.06-6.98 (m, 4H), 3.86 (s, 2H), 3.01-2.83 (m, 4H), m/z=328.9(M+1).

Example 5

1-{4-[4-(2-Benzylamino-ethyl)-phenoxy]-phenyl}-ethanone

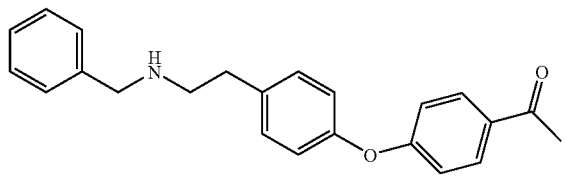

1.4M Methyl Lithium in diethyl ether was added to a dry flask then cooled to 0° C. A solution of 4-[4-(2-Benzylamino-ethyl)-phenoxy]-benzonitrile (2.5 g, 7.6 mmol) (see example 4) in dry tetrahydrofuran (25 mL) was added dropwise to the reaction then stirred at 0° C. for 60 minutes. 3M Sulfuric Acid (12.7 mL, 38 mmol) was added dropwise then the reaction was heated at 50° C. for 3 hours. The reaction was cooled to room temperature then poured into saturated aqueous sodium bicarbonate solution then extracted with dichloromethane (3×75 mL). The combined dichloromethane extracts were dried over sodium chloride/magnesium sulfate, filtered, and concentrated on a rotary evaporator to yield 3.1 g of crude product, which was purified by flash column chromatography on silica gel eluting with ethanol in dichloromethane to yield 1-{4-[4-(2-Benzylamino-ethyl)-phenoxy]-phenyl}-ethanone (0.6 g) which was used directly in the next step.

Example 6

Acetic acid 4-[4-(2-benzylamino-ethyl)-phenoxy]-phenyl ester

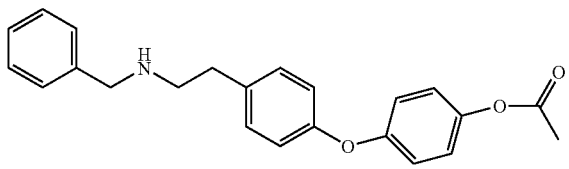

Metachloroperbenzoic acid (0.23 g) was added to a solution of 1-{4-[4-(2-benzylamino-ethyl)-phenoxy]-phenyl}-ethanone (0.36 g) in chloroform (25 mL) while stirring at room temperature. Stirring was continued overnight then the reaction was diluted with dichloromethane, washed with saturated aqueous sodium thiosulfate, dried over sodium chloride/magnesium sulfate, filtered, and concentrated on a rotary evaporator. The residue was diluted with methanol (5 mL) and saturated aqueous sodium bicarbonate (5 mL) then stirred overnight at room temperature. The methanol was removed on a rotary evaporator and the pH of the residue was adjusted to 7-8 then extracted with dichloromethane (3×30 mL). The combined dichloromethane extracts were dried over sodium chloride/magnesium sulfate, filtered, and concentrated on a rotary evaporator to yield 0.4 g of crude product, which was purified by flash column chromatography on silica gel eluting with ethanol in dichloromethane to yield Acetic acid 4-[4-(2-benzylamino-ethyl)-phenoxy]-phenyl ester (117 mg), $^1$H NMR (CDCl3, 300.00 MHz): 8.01-7.93 (m, 2H), 7.42-7.21 (m, 7H), 7.06-6.97 (m, 4H), 3.87 (s, 2H), 3.02-2.94 (m, 4H), 2.61 (s, 3H); m/z=361.85 (M+1).

Example 7

Step 1

4-Mercapto-benzaldehyde

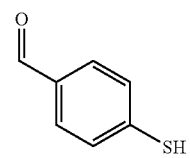

Combine 2-methyl-2-propanethiol sodium salt (2.9 g, 26.3 mmol) and 4-(methylthio)benzaldehyde (2.0 g, 13.2 mmol)

with dimehtylformamide (40 mL) in a dry flask then heat at 160° C. for 4 hours. Cooled to room temperature, poured into 3N aqueous hydrochloric acid (400 mL) then extracted with dichloromethane (3×75 mL). The combined dichloromethane extracts were dried over sodium chloride/magnesium sulfate, filtered, and concentrated on a rotary evaporator to yield the crude product (3 g). The crude product was purified by flash column chromatography on silica gel eluting with ethyl acetate and hexanes to yield 4-mercapto-benzaldehyde (0.7 g): ¹H NMR (DMSO-D6, 300.00 MHz): 9.9 (s, 1H), 7.7 (d, 2H), 7.5 (d, 2H).

Step 2

6-(4-Formyl-phenylsulfanyl)-nicotinamide

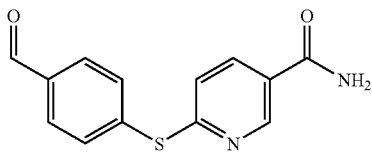

Combine 4-mercapto-benzaldehyde (0.45 g, 3.3 mmol), 6-chloro-nicotinamide (0.52 g, 3.3 mmol), potassium carbonate (0.7 g, 5.1 mmol), and dimehtylformamide (15 mL) then heat at 70° C. overnight. Cool to room temperature, pour into water, and then extract with dichloromethane (3×75 mL). The combined dichloromethane extracts were dried over sodium chloride/magnesium sulfate, filtered, and concentrated on a rotary evaporator to yield the crude product (1 g). The crude product was purified by flash column chromatography on silica gel eluting with 10% aqueous ammonium hydroxide in ethanol and chloroform to yield 6-(4-formyl-phenylsulfanyl)-nicotinamide (120 mg). ¹H NMR (DMSO-D6, 300.00 MHz): 10.08 (s, 1H), 8.91 (dd, 1H, J=2.3, 0.7 Hz), 8.18-8.12 (m, 2H), 8.03-7.98 (m, 2H), 7.83-7.78 (m, 2H), 7.61 (s, 1H), 7.34 (dd, 1H, J=8.4, 0.8 Hz).

Step 3

6-[4-(Benzylamino-methyl)-phenylsulfanyl]-nicotinamide

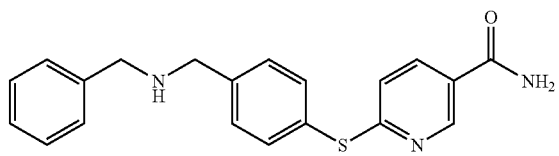

Combine benzylamine (17 mg, 0.16 mmol), 6-(4-formyl-phenylsulfanyl)-nicotinamide (40 mg, 0.16 mmol), 3 Å molecular sieves (0.1 g), and methanol (3 mL) and stir overnight at room temperature. Filter off the sieves then add sodium borohydride (25 mg, 0.64 mmol) to the reaction and stirred at room temperature for 1 hour. Pour the reaction into water then extract with ethyl acetate (3×10 mL). The combined ethyl acetate extracts were dried over sodium chloride/magnesium sulfate, filtered, and concentrated on a rotary evaporator to yield the crude product (50 mg). The crude product was purified by flash column chromatography on silica gel eluting with 10% aqueous ammonium hydroxide in ethanol and chloroform to yield 6-[4-(benzylamino-methyl)-phenylsulfanyl]-nicotinamide, (24 mg): m/z=349.99(M+1); ¹H NMR (MeOD, 300.00 MHz): (8.84 (dd, 1H, J=2.3, 1.0 Hz), 8.02 (dd, 1H, J=8.6, 2.3 Hz), 7.66-7.49 (m, 4H), 7.66-7.49 (m, 4H), 7.42-7.34 (m, 5H), 6.99-6.92 (m, 1H), 3.88-3.77 (m, 4H). HPLC=99% @ 5.82 minutes (5/95 to 95/5 ACN/(0.1% TFA in water) over 10 minutes, Zorbax SB-Phenyl 4.6 mm×15 cm×5 micron, λ=254 nM.

By the method of Example 7 the following compounds were prepared, isolated as the free base except where noted:

| | | Data | |
|---|---|---|---|
| | | | HPLC(5/95 to 95/5 ACN/(0.1% TFA in water) over 10 minutes, Zorbax SB-Phenyl 4.6 mm × 15 cm × 5 micron, λ = 254 nM |
| | | Mass spectrum (ion spray): | |
| Example | Name | m/z (M + 1) | Purity | Retention Time (minutes) |
| 8 | 6-{4-[(3-Methyl-butylamino)-methyl]-phenylsulfanyl}-nicotinamide | 330.04 | 94 | 5.87 |
| 9-1 | 6-{4-[(2-Pyridin-4-yl-ethylamino)-methyl]-phenylsulfanyl}-nicotinamide | 365.00 | 97 | 5.49 |
| 9-2 | 6-[4-(Phenethylamino-methyl)-phenylsulfanyl]-nicotinamide | 364.02 | 99 | 5.92 |
| 10 | 6-{4-[(Cyclopropylmethyl-amino)-methyl]-phenylsulfanyl}-nicotinamide | 314.03 | 100 | 5.67 |
| 11 | 6-{4-[(2-Thiophen-2-yl-ethylamino)-methyl]-phenylsulfanyl}-nicotinamide | 369.96 | 100 | 5.67 |
| 12 | 6-{4-[(3-Phenyl-propylamino)-methyl]-phenylsulfanyl}-nicotinamide | 378.01 | 99 | 6.01 |
| 13 | 6-{4-[(3-Methyl-butylamino)-methyl]-phenylsulfanyl}-nicotinamide | 330.04 | 99 | 5.85 |

Example 14

4-[4-(Phenethylamino-methyl)-benzenesulfonyl]-benzamide

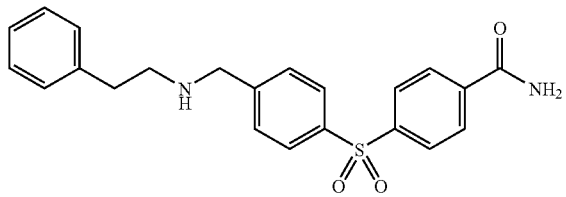

Add a solution of oxone (0.18 g, 0.29 mmol) in water (2 mL) was added to a solution of 4-[4-(phenethylamino-methyl)-phenylsulfanyl]-benzamide (50 mg, 0.14 mmol), 1N aqueous hydrochloric acid (0.14 mL), and tetrahydrofuran (2 mL) at room temperature. Stir overnight at room temperature, pour into saturated aqueous sodium bisulfite, and then extract with ethyl acetate (3×50 mL). The combined ethyl acetate extracts were washed with saturated aqueous sodium bicarbonate solution, water, and brine then dried over sodium chloride/magnesium sulfate. Filter, and concentrate on a rotary evaporator to yield 100 mg of the crude product.

The crude product is purified by flash column chromatography on silica gel eluting with (0.2% conc. ammonium hydroxide/2% ethanol) to (2% conc. ammonium hydroxide/20% ethanol) in chloroform to yield 4-[4-(Phenethylamino-methyl)-benzenesulfonyl]-benzamide, (15 mg): ¹H NMR (DMSO-D6, 300.00 MHz): 9.06-9.01 (m, 1H), 8.50 (dd, 1H, J=8.1, 2.1 Hz), 8.31 (dd, 2H, J=8.2, 0.7 Hz), 7.96-7.81 (m, 3H), 7.61 (d, 2H, J=8.2 Hz), 7.32-7.15 (m, 6H), 3.88-3.82 (m, 2H), 2.78-2.71 (m, 4H); m/z=396.03(M+1); HPLC=90% @ 5.81 minutes (5/95 to 95/5 ACN/(0.1% TFA in water) over 10 minutes, Zorbax SB-Phenyl 4.6 mm×15 cm×5 micron, λ=254 nM.

Example 15

4-[4-(Phenethylamino-methyl)-benzenesulfinyl]-benzamide,

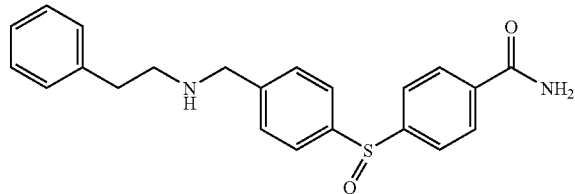

Sodium periodate (43 mg) was added to a solution of 4-[4-(phenethylamino-methyl)-phenylsulfanyl]-benzamide (73 mg, 0.2 mmol), water (10 mL), and methane sulfonic acid (39 mg, 0.4 mmol) while stirring at room temperature. After 1 and 2 hours, and an additional equivalent of sodium periodate (43 mg) and continue to stir at room temperature. Pour the reaction into saturated aqueous sodium bicarbonate solution then extract with ethyl acetate (3×50 mL). The combined ethyl acetate extracts were dried over sodium chloride/magnesium sulfate, filtered, and concentrated on a rotary evaporator to yield the crude product (60 mg). The crude product was purified by flash column chromatography on silica gel eluting with 10% aqueous ammonium hydroxide in ethanol and chloroform to yield 4-[4-(Phenethylamino-methyl)-benzenesulfinyl]-benzamide (26 mg): ¹H NMR (DMSO-D6, 300.00 MHz): 8.98 (d, 1H, J=1.3 Hz), 8.46 (dd, 1H, J=7.9, 2.2 Hz), 8.23 (s, 1H), 8.09 (d, 1H, J=8.3 Hz), 7.75-7.66 (m, 4H), 7.49 (d, 2H, J=8.3 Hz), 7.30-7.15 (m, 5H), 3.76 (s, 2H), 2.75-2.70 (m, 4H); m/z=380.04(M+1); HPLC=100% @ 5.67 minutes (5/95 to 95/5 ACN/(0.1% TFA in water) over 10 minutes, Zorbax SB-Phenyl 4.6 mm×15 cm×5 micron, λ=254 nM.

Example 16

Step 1

6-(4-Cyanomethyl-phenylamino)-nicotinamide

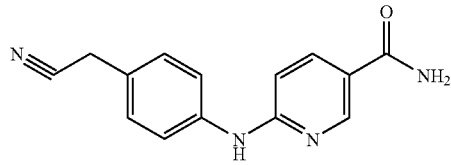

Combine 4-aminophenylacetonitrile (5.0 g, 37.9 mmol) and 6-chloro-nicotinamide (6.3 g, 40.3 mmol) in a flask and heat at 150° C. for 5 hours. Cool, dissolve the residue in methanol, dilute with ethyl acetate, then wash with saturated aqueous sodium bicarbonate solution. Dry the organic layer over sodium chloride/magnesium sulfate, filtered, and concentrated on a rotary evaporator to yield the crude product (10 g). The crude product was purified by flash column chromatography on silica gel eluting with 10% aqueous ammonium hydroxide in ethanol and chloroform to yield 6-(4-cyanomethyl-phenylamino)-nicotinamide. Triturate the resulting solid with hot isopropanol, collect the precipitate to yield 6-(4-cyanomethyl-phenylamino)-nicotinamide (1.8 g): ¹H NMR (DMSO-D6, 300.00 MHz): 9.48 (s, 1H), 8.69 (d, 1H, J=2.1 Hz), 8.03-7.71 (m, 4H), 7.31-7.21 (m, 3H), 6.85 (d, 1H, J=8.8 Hz), 3.97 (s, 2H).

Step 2

6-[4-(2-Amino-ethyl)-phenylamino]-nicotinamide

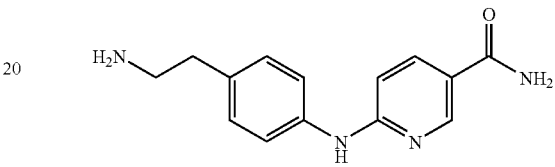

Combine 6-(4-cyanomethyl-phenylamino)-nicotinamide (1.8 g), raney nickel (350 mg), tetrahydrofuran (50 mL), and methanol (100 mL) then hydrogenated at 60 PSIG at 40° C. overnight. Filter off catalyst then concentrate on a rotary evaporator to yield 6-[4-(2-amino-ethyl)-phenylamino]-nicotinamide (1.9 g).

Example 17

6-[4-(2-Benzylamino-ethyl)-phenylamino]-nicotinamide

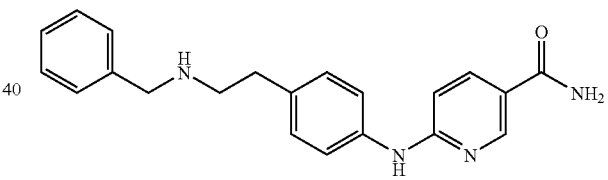

Combine 6-[4-(2-amino-ethyl)-phenylamino]-nicotinamide (200 mg, 0.78 mmol) (step 2, Example 16), benzaldehyde (83 mg, 0.78 mmol), 3 Å molecular sieves (0.2 g), and methanol (10 mL) and stir overnight at room temperature. Filter off the sieves then add sodium borohydride (0.4 mg) to the reaction and stirred at room temperature for 4 hours. Add water (20 mL) then extract with dicholormethane (3×50 mL). Dry the dichloromethane extracts with sodium chloride/magnesium sulfate, filter, then concentrate on a rotary evaporator to yield 0.2 g of the crude product. The crude product is purified by flash column chromatography on silica gel eluting with 10% conc. ammonium hydroxide in ethanol and chloroform to yield 6-[4-(2-Benzylamino-ethyl)-phenylamino]-nicotinamide (24 mg): ¹H NMR (MeOD, 300.00 MHz): 8.66 (d, 1H, J=1.8 Hz), 8.00 (dd, 1H, J=9.0, 2.4 Hz), 7.55-7.15 (m, 10H), 6.81 (d, 1H, J=8.8 Hz), 3.80 (s, 2H), 3.38 (m, 1H), 2.84 (m, 5H); m/z=347.01(M+1); HPLC=95% @ 5.54 minutes (5/95 to 95/5 ACN/(0.1% TFA in water) over 10 minutes, Zorbax SB-Phenyl 4.6 mm×15 cm×5 micron, λ=254 nM.

By the method of Example 17 the following compounds were prepared, isolated as the free base except where noted:

| Example | Name | Data Mass spectrum (ion spray): m/z (M + 1) | HPLC(5/95 to 95/5 ACN/(0.1% TFA in water) over 10 minutes, Zorbax SB-Phenyl 4.6 mm × 15 cm × 5 micron, λ = 254 nM Purity | Retention Time (minutes) |
|---|---|---|---|---|
| 18 | 6-{4-[2-(Cyclohexylmethyl-amino)-ethyl]-phenyl-amino}-nicotinamide | 353.06 | 97 | 5.68 |
| 19 | 6-{4-[(2-Pyridin-4-yl-ethylamino)-methyl]-phenylsulfanyl}-nicotinamide | 327.05 | 99 | 5.60 |

By the method of Example 15, 16, and 17 the following compounds were prepared using 4-aminobenzonitrile as starting material:

| Example | Name | Data Mass spectrum (ion spray): m/z (M + 1) | HPLC(5/95 to 95/5 ACN/(0.1% TFA in water) over 10 minutes, Zorbax SB-Phenyl 4.6 mm × 15 cm × 5 micron, λ = 254 nM Purity | Retention Time (minutes) |
|---|---|---|---|---|
| 20 | 6-[4-(Benzylamino-methyl)-phenylamino]-nicotinamide | 332.99 | 5.55 | 701 |
| 21 | 6-{4-[(Cyclohexylmethyl-amino)-methyl]-phenylamino}-nicotinamide | 339.04 | 5.67 | 706 |
| 22 | 6-[4-(Phenethylamino-methyl)-phenylamino]-nicotinamide | 347.02 | 5.66 | 704 |
| 23 | 6-{4-[(3-Methyl-butylamino)-methyl]-phenylamino}-nicotinamide | 313.05 | 5.57 | 708 |

Example 24

Step 1

[2-(4-Hydroxy-phenyl)-ethyl]-carbamic acid tert-butyl ester

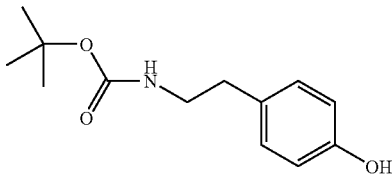

Combine di-tert-butyl dicarbonate (29.1 g, 133.6 mmol), tyramine (15 g, 109.5 mmol), and tetrahydrofuran (750 mL) and stir at room temperature for 18 hours. Concentrate on a rotary evaporator to yield the crude product. The crude product is purified by flash column chromatography on silica gel eluting with 20% ethyl acetate in hexanes to yield [2-(4-hydroxy-phenyl)-ethyl]-carbamic acid tert-butyl ester (23.5 g): $^1$H NMR (CDCl3, 300.00 MHz): 7.04 (d, 2H, J=8.4 Hz), 6.82 (d, 2H, J=8.4 Hz), 4.68 (s, 1H), 3.36 (d, 2H, J=5.3 Hz), 2.74 (m, 2H), 1.47 (s, 9H).

Step 2

{2-[4-(4-Nitro-phenoxy)-phenyl]-ethyl}-carbamic acid tert-butyl ester

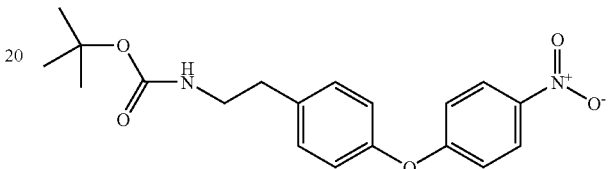

Combine [2-(4-Hydroxy-phenyl)-ethyl]-carbamic acid tert-butyl ester (1.0 g, 4.2 mmol), 4-fluoronitrobenzene (0.6 g, 4.2 mmol), cesium carbonate (2.7 g, 8.4 mmol), and N,N-dimethylformamide (35 mL), stir and heat at 100° C. for 18 hours. Cool to room temperature and evaporate on a rotary evaporator to yield the crude product (9.5 g). The crude product is purified by flash column chromatography on silica gel eluting with (10% conc. ammonium hydroxide in ethanol) and chloroform to yield {2-[4-(4-nitro-phenoxy)-phenyl]-ethyl}-carbamic acid tert-butyl ester (1.3 g): $^1$H NMR (CDCl3, 300.00 MHz): 8.23 (d, 2H, J=9.2 Hz), 7.32-7.25 (m, 2H), 7.10-7.00 (m, 4H), 4.63 (s, 1H), 3.43 (m, 2H), 2.86 (t, 2H, J=7.0 Hz), 1.48 (s, 9H).

Step 3

{2-[4-(4-Amino-phenoxy)-phenyl]-ethyl}-carbamic acid tert-butyl ester

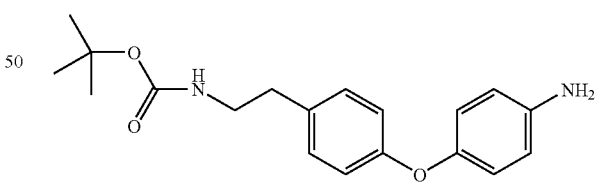

Combine {2-[4-(4-nitro-phenoxy)-phenyl]-ethyl}-carbamic acid tert-butyl ester (1.3 g), 5% Pd/C (100 mg), and methanol (50 mL) then hydrogenated at 40 PSIG at room temperature for 2 hours. Filter off catalyst then concentrate on a rotary evaporator to yield {2-[4-(4-Amino-phenoxy)-phenyl]-ethyl}-carbamic acid tert-butyl ester (1.2 g): $^1$H NMR (CDCl3, 300.00 MHz): 7.12 (d, 2H, J=8.4 Hz), 6.89 (d, 4H, J=8.8 Hz), 6.72 (d, 2H, J=8.8 Hz), 4.61 (s, 1H), 3.42-3.32 (m, 2H), 2.77 (t, 2H, J=7.0 Hz), 1.46 (s, 9H).

Step 4

{2-[4-(4-Acetylamino-phenoxy)-phenyl]-ethyl}-carbamic acid tert-butyl ester

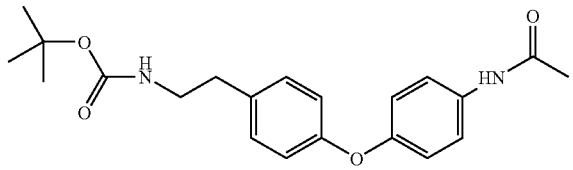

Add a solution of {2-[4-(4-Amino-phenoxy)-phenyl]-ethyl}-carbamic acid tert-butyl ester (1.2 g, 3.66 mmol) in dichloromethane (25 mL) dropwise to a solution of acetyl chloride (0.35 g, 4.50 mmol) in dichloromethane (125 mL) at room temperature. Upon complete addition of the amine, add triethylamine (0.74 g, 7.32 mmol) and a crystal of DMAP to the reaction and stirred at room temperature for 18 hours. Add an additional 65 uL of acetyl chloride to the reaction and stir an additional 2 hours. Pour the reaction into saturated aqueous sodium bicarbonate then extract with dichloromethane (3×100 mL). Dry the dichloromethane extracts over sodium chloride/magnesium sulfate, filter, then concentrate on a rotary evaporator to yield 1.3 g of the crude product. The crude product is purified by flash column chromatography on silica gel eluting with ethyl acetate and hexanes to yield {2-[4-(4-acetylamino-phenoxy)-phenyl]-ethyl}-carbamic acid tert-butyl ester (1.2 g): $^1$H NMR (CDCl3, 300.00 MHz): 8.00 (s, 1H), 7.49 (d, 2H, J=8.8 Hz), 7.13 (d, 2H, J=8.4 Hz), 6.98-6.89 (m, 4H), 4.69 (s, 1H), 3.37 (d, 2H, J=6.2 Hz), 2.77 (t, 2H, J=7.0 Hz), 2.18 (s, 3H), 1.46 (s, 9H).

Example 25

N-{4-[4-(2-Amino-ethyl)-phenoxy]-phenyl}-acetamide

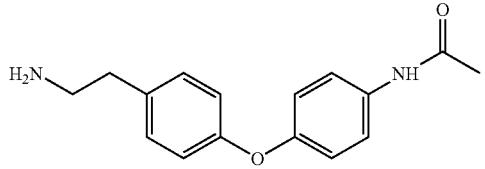

Add trifluoroacetic acid (10 mL) dropwise to a solution of {2-[4-(4-acetylamino-phenoxy)-phenyl]-ethyl}-carbamic acid tert-butyl ester (3.7 g, 10 mmol) in dichloromethane (50 mL) at 0° C. Warm to room temperature and stir overnight. Concentrate on a rotary evaporator, dissolve residue in methanol then apply to a strong cation exchange column (Varian, 0.79 meq/g), and wash with methanol. Elute the product with 2M ammonia in methanol then concentrate on a rotary evaporator to yield N-{4-[4-(2-amino-ethyl)-phenoxy]-phenyl}-acetamide (2.3 g): $^1$H NMR (DMSO-D6, 300.00 MHz): 9.97 (s, 1H), 7.58 (d, 2H, J=8.8 Hz), 7.19 (d, 2H, J=7.9 Hz), 6.92 (dd, 4H, J=21.3, 8.1 Hz), 3.60-3.05 (m, 3H), 2.73-2.55 (m, 3H), 2.04 (s, 3H).

Example 26

N-{4-[4-(2-Benzylamino-ethyl)-phenoxy]-phenyl}-acetamide

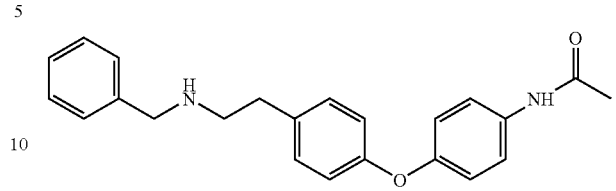

Combine N-{4-[4-(2-amino-ethyl)-phenoxy]-phenyl}-acetamide (100 mg, 0.37 mmol), benzaldehyde (47 mg, 0.44 mmol), 3 Å molecular sieves (300 mg), and methanol (3 mL) and stir overnight at room temperature. Filter off the sieves then add sodium borohydride (28 mg) to the reaction and stirred at room temperature for 2 hours. Concentrate on a rotary evaporator and purified by radial chromatography on silica gel eluting with 10% conc. ammonium hydroxide in ethanol and chloroform to yield N-{4-[4-(2-benzylamino-ethyl)-phenoxy]-phenyl}-acetamide, (61 mg): $^1$H NMR (CDCl3, 300.00 MHz): 7.51-6.88 (m, 13H), 3.84 (s, 2H), 2.97-2.78 (m, 4H), 2.21 (s, 3H), 1.55 (s, 1H); HPLC=99% (5/95 to 95/5 ACN/(0.1% TFA in water) over 10 minutes, Zorbax SB-Phenyl 4.6 mm×15 cm×5 micron, λ=254 nM.

By the method of Example 26 the following compounds were prepared, isolated as the free base except where noted:

| | | Data | |
|---|---|---|---|
| | | Mass spectrum (ion spray): m/z (M + 1) | HPLC(5/95 to 95/5 ACN/(0.1% TFA in water) over 10 minutes, Zorbax SB-Phenyl 4.6 mm × 15 cm × 5 micron, λ = 254 nM |
| Example | Name | | Purity | Retention Time (minutes) |
| 27 | N-{4-[4-(2-Hexylamino-ethyl)-phenoxy]-phenyl}-acetamide | 355.16 | 91 | |
| 28 | N-[4-(4-{2-[(Thiophen-2-ylmethyl)-amino]-ethyl}-phenoxy)-phenyl]-acetamide | 367.07 | 99 | |
| 29 | N-(4-{4-[2-(3-Phenyl-propylamino)-ethyl]-phenoxy}-phenyl)-acetamide | 389.14 | 97 | |
| 30 | N-(4-{4-[2-(2-Cyclohexyl-ethylamino)-ethyl]-phenoxy}-phenyl)-acetamide | 381.17 | 97 | |
| 31 | N-{4-[4-(2-Phenethylamino-ethyl)-phenoxy]-phenyl}-acetamide | 375.12 | 81 | |
| 32 | N-{4-[4-(2-Propylamino-ethyl)-phenoxy]-phenyl}-acetamide | 353.1 | 92 | |
| 33 | N-{4-[4-(2-Pentylamino-ethyl)-phenoxy]-phenyl}-acetamide | 341.1 | 81 | |
| 34 | N-(4-{4-[2-(Cyclohexylmethyl-amino)-ethyl]-phenoxy}-phenyl)-acetamide | 367.2 | 97 | |

-continued

| Example | Name | Mass spectrum (ion spray): m/z (M + 1) | Purity | HPLC(5/95 to 95/5 ACN/(0.1% TFA in water) over 10 minutes, Zorbax SB-Phenyl 4.6 mm × 15 cm × 5 micron, λ = 254 nM Retention Time (minutes) |
|---|---|---|---|---|
| 35 | N-(4-{4-[2-(2-Trifluoromethyl-benzylamino)-ethyl]-phenoxy}-phenyl)-acetamide | 429.1 | 92 | |
| 36 | N-[4-(4-{2-[(Furan-2-ylmethyl)-amino]-ethyl}-phenoxy)-phenyl]-acetamide | 351.1 | 95 | |
| 37 | N-(4-{4-[2-(3-Chloro-benzylamino)-ethyl]-phenoxy}-phenyl)-acetamide | 395.1 | 98 | |
| 38 | N-{4-[4-(2-Isobutylamino-ethyl)-phenoxy]-phenyl}-acetamide | 327.1 | 98 | |
| 39 | N-{4-[4-(2-Cyclohexylamino-ethyl)-phenoxy]-phenyl}-acetamide | 353.1 | 99 | |
| 40 | N-(4-{4-[2-(2-Methyl-benzylamino)-ethyl]-phenoxy}-phenyl)-acetamide | 375.1 | 99 | |
| 41 | N-(4-{4-[2-(3-Fluoro-benzylamino)-ethyl]-phenoxy}-phenyl)-acetamide | 379.1 | 87 | |
| 42 | N-[4-(4-{2-[(3-Methyl-thiophen-2-ylmethyl)-amino]-ethyl}-phenoxy)-phenyl]-acetamide | 381.1 | 99 | |
| 43 | N-(4-{4-[2-(3-Methyl-butylamino)-ethyl]-phenoxy}-phenyl)-acetamide | 341.2 | 95 | |
| 44 | N-(4-{4-[2-(3,5-Difluoro-benzylamino)-ethyl]-phenoxy}-phenyl)-acetamide | 397.1 | 86 | |
| 45 | N-[4-(4-{2-[(Pyridin-3-ylmethyl)-amino]-ethyl}-phenoxy)-phenyl]-acetamide | 362.1 | 99 | |

Example 46

Step 1

4-(2-Benzylamino-ethyl)-phenol

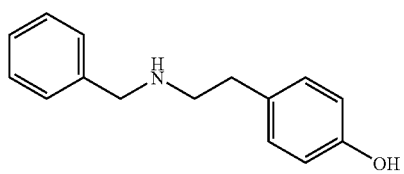

Combine tyramine (3.0 g, 3.3 mmol), benzaldehyde (3.0, 2.2 mmol), 3 Å molecular sieves (5 g), ethanol (3 mL) and stir overnight at room temperature. Filter off the sieves then add sodium borohydride (2.5 g) to the reaction at 0° C. then stirred at room temperature overnight. Concentrate on a rotary evaporator, take up residue in water, and then extract with dichloromethane (3×100 mL). Dry the dichloromethane extracts over sodium chloride/magnesium sulfate, filter, then concentrate on a rotary evaporator to yield 4.3 g of the crude product. The crude product is purified by flash column chromatography on silica gel eluting with 10% conc. ammonium hydroxide in ethanol and chloroform to yield 4-(2-benzylamino-ethyl)-phenol (2.6 g): $^1$H NMR (DMSO-D6, 300.00 MHz): 9.17 (s, 1H), 7.31 (m, 5H), 6.99 (d, 2H, J=8.4 Hz), 6.67 (d, 2H, J=8.8 Hz), 3.70 (s, 2H), 2.64 (m, 4H), 2.11 (s, 1H).

Step 2

Benzyl-[2-(4-hydroxy-phenyl)-ethyl]-carbamic acid tert-butyl ester

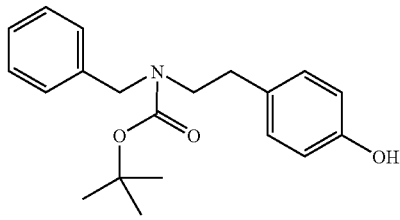

Combine di-tert-butyl dicarbonate (3.1 g, 14.0 mmol), 4-(2-benzylamino-ethyl)-phenol (2.6 g, 11.5 mmol), and tetrahydrofuran (75 mL) and stir at room temperature for 18 hours. Concentrate on a rotary evaporator to yield the crude product. The crude product is purified by flash column chromatography on silica gel eluting with 20% ethyl acetate in hexanes to yield benzyl-[2-(4-hydroxy-phenyl)-ethyl]-carbamic acid tert-butyl ester (2.7 g): $^1$H NMR (CDCl3, 300.00 MHz): 7.01-6.16 (m, 9H), 5.44 (s, 1H), 3.95 (s, 2H), 2.89 (m, 2H), 2.26 (m, 2H), 1.06 (s, 9H).

Step 3

Benzyl-{2-[4-(4-nitro-phenoxy)-phenyl]-ethyl}-carbamic acid tert-butyl ester

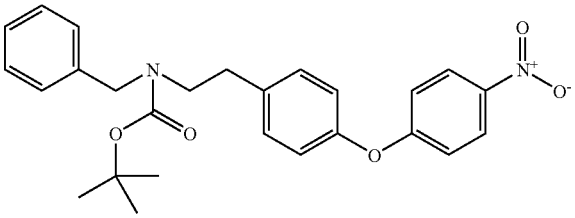

Combine benzyl-[2-(4-hydroxy-phenyl)-ethyl]-carbamic acid tert-butyl ester (2.7 g, 8.3 mmol), 4-fluoronitrobenzene (1.2 g, 8.3 mmol), cesium carbonate (5.4 g, 16.6 mmol), and N,N-dimethylformamide (70 mL), stir at room temperature overnight. Pour the reaction into brine then extract with ethyl acetate (3×100 mL). The combined ethyl acetate extracts were dried over sodium chloride/magnesium sulfate, filtered, and concentrated on a rotary evaporator to yield the crude product (3.5 g). The crude product was purified by flash column chromatography on silica gel eluting with ethyl acetate and hexanes to yield benzyl-{2-[4-(4-nitro-phenoxy)-phenyl]-ethyl}-carbamic acid tert-butyl ester (2.7 g): ¹H NMR (CDCl3, 300.00 MHz): 8.22 (d, 2H, J=9.2 Hz), 7.44-6.95 (m, 11H), 4.44 (m, 2H), 3.44 (m, 2H), 2.84 (m, 2H), 1.52 (m, 9H).

Step 4

{2-[4-(4-Amino-phenoxy)-phenyl]-ethyl}-benzyl-carbamic acid tert-butyl ester

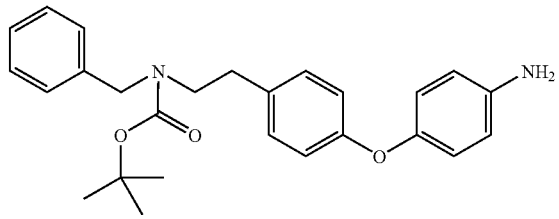

Combine benzyl-{2-[4-(4-nitro-phenoxy)-phenyl]-ethyl}-carbamic acid tert-butyl ester (2.5 g), 5% Pd/C (200 mg), and methanol (100 mL) then hydrogenated at 40 PSIG at room temperature for 2 hours. Filter off catalyst then concentrate on a rotary evaporator to yield {2-[4-(4-amino-phenoxy)-phenyl]-ethyl}-benzyl-carbamic acid tert-butyl ester (2.3 g): ¹H NMR (CDCl3, 300.00 MHz): 7.42-6.70 (m, 13H), 4.41 (m, 2H), 3.39 (m, 2H), 2.77 (m, 2H), 1.52 (s, 9H).

Step 5

4-[4-(2-Benzylamino-ethyl)-phenoxy]-phenylamine

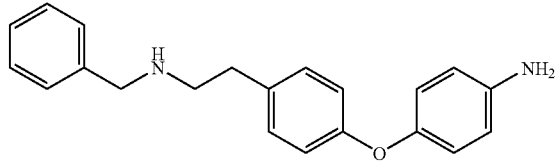

Add trifluoroacetic acid (0.24 mL) dropwise to a solution of {2-[4-(4-Amino-phenoxy)-phenyl]-ethyl}-benzyl-carbamic acid tert-butyl ester (100 mg, 0.24 mmol) in dichloromethane (5 mL) at room temperature and stir overnight. Concentrate on a rotary evaporator, dilute with saturated aqueous sodium bicarbonate then extract with dichloromethane (3×50 mL). Dry the dichloromethane extracts over sodium chloride/magnesium sulfate, filter, then concentrate on a rotary evaporator to yield 4-[4-(2-benzylamino-ethyl)-phenoxy]-phenylamine, (38 mg): ¹H NMR (CDCl3, 300.00 MHz): 7.42-6.67 (m, 14H), 3.86 (s, 2H), 3.61 (s, 2H), 2.88 (m, 4H); m/z=319.2(M+1); HPLC=97% (5/95 to 95/5 ACN/(0.1% TFA in water) over 10 minutes, Zorbax SB-Phenyl 4.6 mm×15 cm×5 micron, λ-254 nM.

Step 6

N-{4-[4-(2-Benzylamino-ethyl)-phenoxy]-phenyl}-benzamide

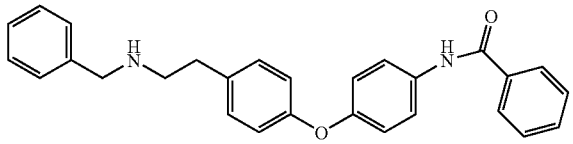

Add a solution of {2-[4-(4-amino-phenoxy)-phenyl]-ethyl}-benzyl-carbamic acid tert-butyl ester (100 mg, 0.24 mmol) in dichloromethane (5 mL) dropwise to a solution of benzoyl chloride (40 mg, 0.29 mmol) in dichloromethane (5 mL) at room temperature. Upon complete addition of the amine, add triethylamine (48 mg, 0.48 mmol) and a crystal of DMAP to the reaction and stirred at room temperature for 18 hours. Concentrate on a rotary evaporator then purify by flash column chromatography on silica gel eluting with ethyl acetate and hexanes to yield {2-[4-(4-benzoylamino-phenoxy)-phenyl]-ethyl}-benzyl-carbamic acid tert-butyl ester (120 mg). Add trifluoroacetic acid (0.23 mL) dropwise to a solution of [4-(4-benzoylamino-phenoxy)-phenyl]-ethyl}-benzyl-carbamic acid tert-butyl ester (120 mg, 0.23 mmol) in dichloromethane (5 mL) at room temperature and stir overnight. Concentrate on a rotary evaporator, dilute with saturated aqueous sodium bicarbonate then extract with dichloromethane (3×50 mL). Dry the dichloromethane extracts over sodium chloride/magnesium sulfate, filter, then concentrate on a rotary evaporator to yield N-{4-[4-(2-benzylamino-ethyl)-phenoxy]-phenyl}-benzamide, (27 mg): ¹H NMR (CDCl3, 300.00 MHz): 7.96-6.93 (m, 18H), 3.85 (s, 2H), 2.99-2.80 (m, 4H), 1.56 (s, 2H); m/z=423.4 (M+1); HPLC=99% (5/95 to 95/5 ACN/(0.1% TFA in water) over 10 minutes, Zorbax SB-Phenyl 4.6 mm×15 cm×5 micron, λ=254 nM.

By the method of Example 46 the following compounds were prepared, isolated as the free base except where noted:

| | | Data | | |
|---|---|---|---|---|
| Example | Name | Mass spectrum (ion spray): m/z (M + 1) | Purity | HPLC(5/95 to 95/5 ACN/(0.1% TFA in water) over 10 minutes, Zorbax SB-Phenyl 4.6 mm × 15 cm × 5 micron, λ = 254 nM Retention Time (minutes) |
| 47 | Morpholine-4-carboxylic acid {4-[4-(2-benzylamino-ethyl)-phenoxy]-phenyl}-amide | 432.5 | 96 | |
| 48 | N-{4-[4-(2-Benzylamino-ethyl)-phenoxy]-phenyl}-2-methoxy-acetamide | 391.1 | 100 | |
| 49 | Furan-2-carboxylic acid {4-[4-(2-benzylamino-ethyl)-phenoxy]-phenyl}-amide | 413.1 | 100 | |
| 50 | Isoxazole-5-carboxylic acid {4-[4-(2-benzylamino-ethyl)-phenoxy]-phenyl}-amide | 414.1 | 80 | |
| 51 | Thiophene-2-carboxylic acid {4-[4-(2-benzylamino-ethyl)-phenoxy]-phenyl}-amide | 429.1 | 100 | |
| 52 | N-{4-[4-(2-Benzylamino-ethyl)-phenoxy]-phenyl}-isonicotinamide | 424.1 | 100 | |
| 53 | 3,5-Dimethyl-isoxazole-4-carboxylic acid {4-[4-(2-benzylamino-ethyl)-phenoxy]-phenyl}-amide | 442.1 | 100 | |
| 54 | 2-tert-Butyl-5-methyl-2H-pyrazole-3-carboxylic acid {4-[4-(2-benzylamino-ethyl)-phenoxy]-phenyl}-amide | 483.2 | 99 | |
| 55 | 5-Methyl-isoxazole-3-carboxylic acid {4-[4-(2-benzylamino-ethyl)-phenoxy]-phenyl}-amide | 428.1 | 100 | |

47

-continued

| Example | Name | Mass spectrum (ion spray): m/z (M + 1) | HPLC(5/95 to 95/5 ACN/(0.1% TFA in water) over 10 minutes, Zorbax SB-Phenyl 4.6 mm × 15 cm × 5 micron, λ = 254 nM | |
|---|---|---|---|---|
| | | | Purity | Retention Time (minutes) |
| 56 | 4-Methyl-[1,2,3]thiadiazole-5-carboxylic acid {4-[4-(2-benzylamino-ethyl)-phenoxy]-phenyl}-amide | 445.1 | 99 | |
| 57 | N-{4-[4-(2-Benzylamino-ethyl)-phenoxy]-phenyl}-3-methylsulfanyl-propionamide | 421.1 | 100 | |
| 58 | Quinoxaline-2-carboxylic acid {4-[4-(2-benzylamino-ethyl)-phenoxy]-phenyl}-amide | 475.1 | 99 | |
| 59 | N-{4-[4-(2-Benzylamino-ethyl)-phenoxy]-phenyl}-nicotinamide | 424.4 | | |
| 60 | Pyridine-2-carboxylic acid {4-[4-(2-benzylamino-ethyl)-phenoxy]-phenyl}-amide | 424.1 | 99 | |

Example 61

Step 1

4-(5-Bromo-pyridin-2-yloxy)-benzaldehyde

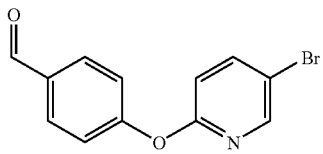

To a solution of 4-hydroxy benzaldehyde (4.22 g, 34.6 mmol) and 2,5-dibromopyridine (8.19 g, 34.6 mmol) in dimethylacetamide (100 mL) is added $K_2CO_3$ (11.95 g, 86.4 mmol) at RT. The reaction mixture is warmed to 130° C. for 8 h. The reaction mixture is then poured into $H_2O$ (200 mL) and saturated $NaHCO_3$ (100 mL), extracted with EtOAc (3×200 mL), and then the combined extracts are washed with saturated $NaHCO_3$, brine, dried over $MgSO_4$, filtered, and concentrated. The mixture is loaded on silica gel, eluted with hexanes with a gradient from 5% of ethyl acetate to 25% of ethyl acetate giving ethyl 4-(5-Bromo-pyridin-2-yloxy)-benzaldehyde (3.50 g, 36%) as a white solid. $^1$NMR (400 MHz, CDCl$_3$) δ ppm: 9.96 (s, 1H), 8.23 (d, J=2.6 Hz, 1H), 7.93-7.90 (m, 2H), 7.83 (ds, J=2.6, 8.4 Hz, 1H), 7.27-7.24 (m, 2H), 6.92 (d, J=7.9 Hz, 1H); MS (ES): [M+H]$^+$ found 277.7.

48

Step 2

[4-(5-Bromo-pyridin-2-yloxy)-benzyl]-(3-methyl-butyl)-amine

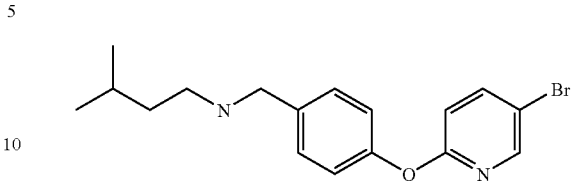

To a solution of 4-(5-Bromo-pyridin-2-yloxy)-benzaldehyde (RH3-A02640-038) (3.501 g, 12.6 mmol) in 1,2-dichloroethane (61 mL) is added isoamylamine (1.65 mL, 14.2 mmol), NaBH(OAc)$_3$ (4.00 g, 18.9 mmol), and acetic acid (1.10 mL, 19.2 mmol). The reaction is stirred overnight. The reaction mixture is then washed with saturated $NaHCO_3$ (2×100 mL), dried over $MgSO_4$, filtered, and concentrated. The mixture is loaded on silica gel, eluted with hexanes with a gradient from 25% of ethyl acetate to 100% of ethyl acetate to give [4-(5-Bromo-pyridin-2-yloxy)-benzyl]-(3-methyl-butyl)-amine (2.18 g, 50%) as a yellow oil. $^1$NMR (400 MHz, CDCl$_3$) δ ppm: 8.21 (d, J=3.1 Hz, 1H), 7.75 (dd, J=2.6, 8.7 Hz, 1H), 7.37-7.34 (m, 2H), 7.09-7.05 (m, 2H), 6.82 (d, J=9.1 Hz, 1H), 2.49 (s, 2H), 2.66 (dd, J=7.6, 7.6 Hz, 2H), 1.67-1.61 (m, 1H), 1.44-1.38 (m, 2H), 1.15 (s br, 1H), 0.90 (d, J=6.6 Hz, 6H); MS (ES): [M+H]$^+$ found 261.7.

Step 3

N-(6-{4-[(3-Methyl-butylamino)-methyl]-phenoxy}-pyridin-3-yl)-acetamide

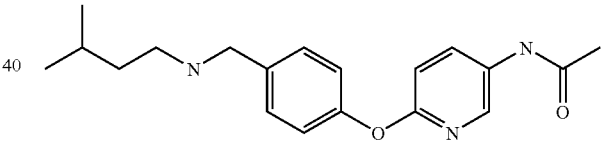

To a solution of [4-(5-Bromo-pyridin-2-yloxy)-benzyl]-(3-methyl-butyl)-amine (0.493 g, 1.411 mmol), acetamide (0.0938 g, 1.588 mmol), and CuI (0.0309 g, 1.622 mmol) in 1,4-dioxane (3.0 ml) is added (+/−)-trans-1,2-diaminocyclohexane (0.020 mL, 1.67 mmol) and $K_2CO_3$ (0.400 g, 0.891 mmol). The reaction mixture is then warmed to 100° C. overnight. Additional amounts of CuI (0.0270 mg, 0.142 mmol) and (+/−)-trans-1,2-diaminocyclohexane (0.020 mL, 1.67 mmol) are added. The reaction mixture is placed in a microwave reactor (CEM Discover, 50W) for 60 min. The mixture is filtered through celite, loaded onto silica gel, and eluted with chloroform with a gradient from 10% of methanol to 30% of methanol to give N-(6-{4-[(3-Methyl-butylamino)-methyl]-phenoxy}-pyridin-3-yl)-acetamide (0.025 g, 5%) as a brown oil. $^1$NMR (400 MHz, CD$_3$OD) δ ppm: 8.30 (d, J=2.7 Hz, 1H), 8.04 (dd, J=2.5, 8.7 Hz, 1H), 7.38 (d, J=8.6 Hz, 2H), 7.07-7.03 (m, 2H), 6.91 (d, J=8.9 Hz, 1H), 3.82 (s, 2H), 2.68 (dd, J=7.7, 8.0 Hz, 2H), 2.18 (s, 3H), 1.70-1.61 (m, 1H), 1.52-1.44 (m, 2H), 0.96 (d, J=6.6 Hz, 6H); MS (ES): [M+H]$^+$ calcd for $C_{19}H_{26}N_3O_2$=328.2025, found 328.2000

Example 62

4-[4-(2-Benzylaminoethyl)phenoxy]benzenesulfonamide

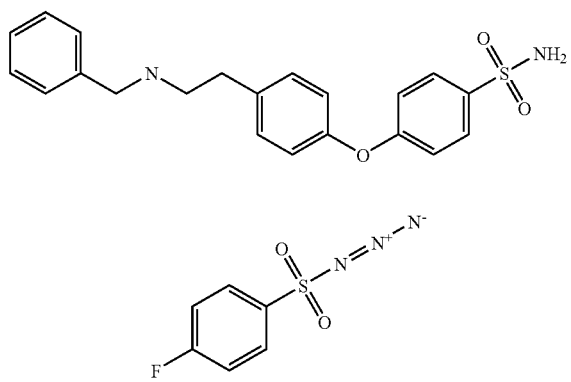

Part A: 4-Fluorobenzenesulfonyl azide

Suspend 4-fluorobenzenesulfonyl chloride (0.500 g, 2.57 mmol) and sodium azide (0.200 g, 3.08 mmol) in acetone. Heat at reflux overnight before concentrating the reaction mixture. Purify by flash 40 chromatography, eluting with 10% ethyl acetate in hexanes to give the title compound: $^1$HNMR (DMSO-$d_6$) δ 7.58 (tt, J=8.04, 2.02 Hz, 2H), 8.12 (td, 4.89, 1.96 Hz, 2H); HPLC [YMC-Pack Pro C-18 (150× 4.6 mm, S-5 microm), acetonitrile in water containing 0.01% concentrated HCl at 1.0 mL/min, 50-99% over 19 min], $t_R$=16.5 min, 92.4% purity.

Part B: {2-[4-(4-Azidosulfonylphenoxy)phenyl]ethyl} carbamic acid tert-butyl ester

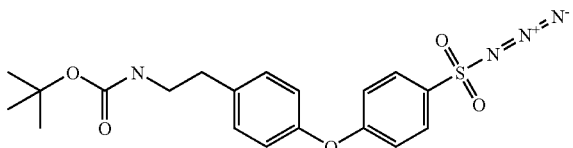

Dissolve [2-(4-hydroxyphenyl)ethyl]carbamic acid tert-butyl ester (0.594 g, 2.50 mmol) in DMF (12.5 mL). Add NaH (80% in mineral oil) (0.083 g, 2.75 mmol). Stir at room temperature for 30 minutes. Add 4-fluorobenzenesulfonyl azide (0.504 g, 2.50 mmol) and heat to 60° C. Remove DMF as an azeotrope with xylenes after 3.75 hours. Purify by flash 40 chromatography, eluting with 30% ethyl acetate in hexanes to give a mixture of (2-(4-(4-fluorobenzenesulfonyl)oxyphenyl)ethyl)carbamic acid tert-butyl ester and the title compound: HPLC [YMC-Pack Pro C-18 (150×4.6 mm, S-5 microm), acetonitrile in water containing 0.01% concentrated HCl at 1.0 mL/min, 50-99% over 19 min], $t_R$=16.1 min, 35% purity; TLC [silica gel 60 $F_{254}$, 5% ethyl acetate in hexanes] $R_f$=0.49.

Part C: 4-[4-(2-Aminoethyl)phenoxy]benzenesulfonyl azide

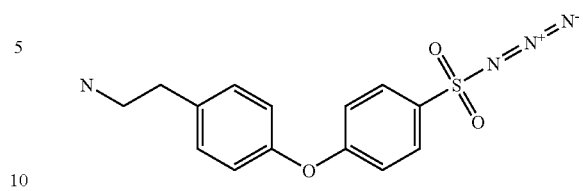

Dissolve the mixture of {2-[4-(4-azidosulfonylphenoxy)phenyl]ethyl} carbamic acid tert-butyl ester (0.291 g, 0.695 mmol) in dichloromethane (12 mL). Add TFA (12 mL) and stir at room temperature for 5 hours. Concentrate the reaction mixture. Load the product onto an SCX column with methanol. Wash the column with methanol then elute with 50% (2.0 M NH$_3$ in methanol) in methanol to give a mixture of 2-4-(4-fluorobenzenesulfonyl)oxyphenyl)ethylamine and the title compound (0.601 g, 98.5%): MS ES$^+$ 336.9 (M+H+ 18(NH$_4$))$^+$; TLC [silica gel 60 $F_{254}$, 30% ethyl acetate,5% (2.0 M NH$_3$ in methanol and 65% hexanes] $R_f$=0.034.

Part D: 4-[4-(2-Benzylaminoethyl)phenoxy]benzenesulfonamide

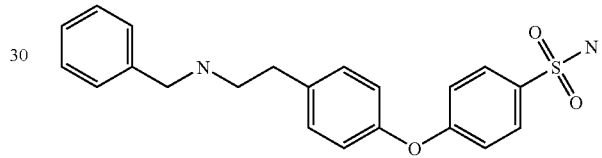

Take up the mixture of 4-[4-(2-aminoethyl)phenoxy] benzenesulfonyl azide (0.210 g, 0.661 mmol) in methanol (9.9 mL). Add benzaldehyde (0.20 mL, 1.98 mmol) and 3 Å molecular sieves. Stir at room temperature overnight. Add NaBH$_4$ (0.075 g, 1.98 mmol) and stir for 1.5 hours. Filter the reaction mixture and purify by flash 40 chromatography, eluting with 3% (2.0 M NH$_3$ in methanol), 30% hexanes and 67% ethyl acetate to give the title compound (0.0696 g, 25.8%): TOF MS ES$^+$ 383.1 (M+H)$^+$, HRMS calcd for $C_{21}H_{23}N_2O_3S$ 383.1429 (M+H)$^+$, found 383.1436, time 0.33 min; TLC [silica gel 60 $F_{254}$, 10% (2.0 M NH$_3$ in methanol) in dichloromethane] $R_f$=0.31.

Example 63

6-(4-Cyano-benzyl)-nicotinamide

Step 1

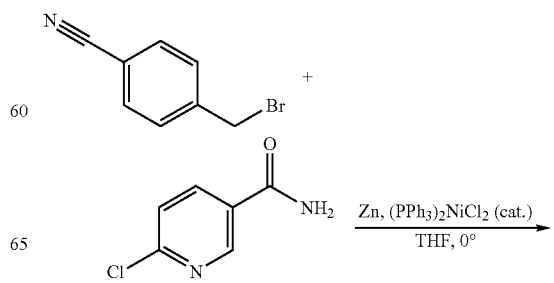

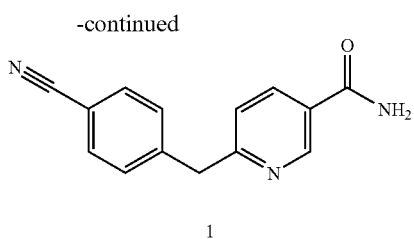

Following the procedure disclosed in *J. Het. Chem* 1999, 36, 445, a solution of 4-cyanobenzyl bromide (1 g, 5.1 mmol) in THF (5 mL) is added to a stirred suspension of Zinc dust (498 mg, 7.5 mmol) in anhydrous THF (7 mL) cooled in an ice bath under a nitrogen atmosphere. The suspension was stirred for 5 hours in an ice bath. In a separate flask, anhydrous THF (26 mL) is added to dichloro-bis-(triphenylphosphine) Nickel II (560 mg, 0.86 mmol) under nitrogen atmosphere at room temperature. 6-chloro-nicotinamide (800 mg, 5.1 mmol) in THF (20 mL) is added to the catalyst; not all material is in solution. After stirring 5 minutes, the zinc dust suspension is allowed to settle, and the solution is added via cannula to the nickel catalyst/nicotinamide mixture, taking care to leave unreacted zinc dust behind. The reaction immediately turns dark purple, and is stirred for 72 hours at room temperature under nitrogen, at which point the reaction is a clear yellow solution. A saturated aqueous solution of ammonium chloride (50 mL) is added and the mixture stirred 20 minutes. The reaction mixture is then washed with 3×50 mL ethyl actetate, and the organics washed with 2×50 mL brine, dried over magnesium sulfate, and evaporated to give a tan solid. The solid is washed with ether, and the ether layer discarded. The remaining material was dried under vaccuum to give 723 mg crude material. The material is purified by flash chromatography on an ISCO (dry pack onto 12 g column; gradient: 40 mL/min, EtOAc 0-15 min, 0-5% MeOH/EtOAc 15-30 min, 5% MeOH/EtOAc 30-35 min). Product is isolated as a white solid, 110 mg, plus an additional 225 mg product contaminated with starting material. This is re-purified as above to give an additional 67 mg product. Total yield 177 mg (15%).

$^1$H NMR (CD$_3$OD): 8.94 (d, 1H, J=3 Hz); 8.20 (dd, 1H, J=7 Hz, 19 Hz); 7.66 (d, 2H, J=19 Hz); 7.45 (m, 3 H); 4.28 (s, 2H)

Step 2

6-(4-Formyl-benzyl)-nicotinamide

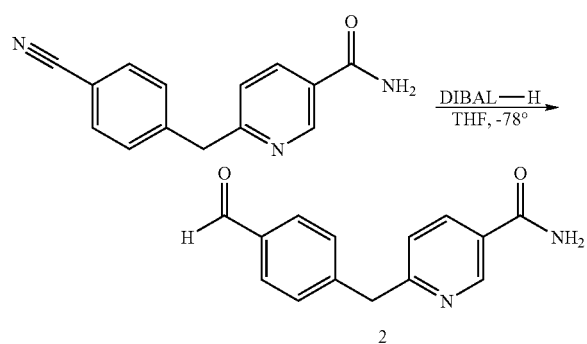

Compound 1 (175 mg) is dissolved in anhydrous THF (15 mL) and cooled to in a dry ice/acetone bath. A 1M solution of DIBAl-H in toluene (1 mL) is added and the reaction is stirred for 1 hour at −78°. After 1 hour, an additional 1 mL DIBAL-H solution is added, and the reaction is placed at −28° overnight. The reaction is then warmed to room temperature, stirred for 3 hours, and treated with an additional 700 uL DIBAL-H solution, at which point no starting nitrile remains. Water is added (25 mL) and the mixture is stirred 5 minutes, then extracted with 3×50 mL ethyl acetate. The organics are washed with 50 mL brine, dried over magnesium sulfate, and evaporated to yield 144 mg crude product. This is purified by flash chromatography on an ISCO (10 g column, 40 mL/min, gradient: EtOAc, 0-10 min; 0-5% MeOH/EtOAc 10-25 minutes) to give 47 mg final product (27% yield).

$^1$H NMR (CD$_3$OD): 9.94 (s, 1H); 9.5 (s, 1H); 8.20 (dd, 1H, J=6 Hz, 20 Hz); 7.85 (d, 2H, J=20 Hz); 7.46 (m, 3H); 4.30 (s, 2H). MS: 241.0 (M+1)

Step 3

6-{4-[(3-Methyl-butylamino)-methyl]-benzyl}-nicotinamide

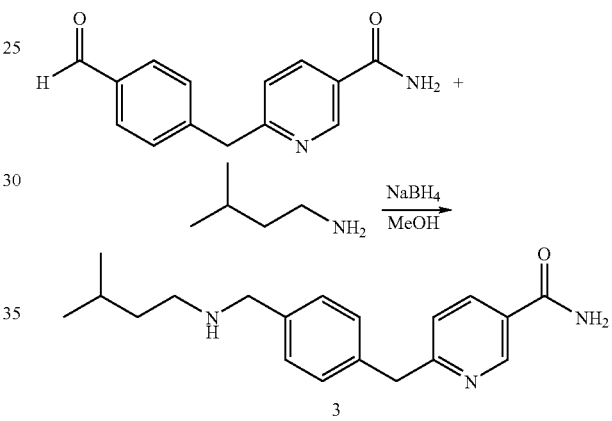

A mixture of aldehyde 2 (22 mg, 90 umol) is dispersed in methanol (2 mL). To this mixture is added 2-methylbutylamine (15 mg, 170 umol); all solid dissolves after 10 minutes of stirring at room temperature. To the stirred solution is added sodium borohydride (14 mg, 370 umol), significant gas evolution is observed. The reaction mixture is then poured onto a 1 g Varian SCX cartridge which has been conditioned with a 5% solution of acetic acid in methanol. The column is rinsed with methanol, then eluted using 2.5 mL of a 2N ammonia solution in methanol, and the organic is evaporated to give 30 mg crude material. This is purified by flash chromatography using an ISCO (4 g column, eluent: 40 mL/min, 1-5% (1N NH$_3$/MeOH)/CH$_2$Cl$_2$, 0-10 min; 5% (1N NH$_3$/MeOH)/CH$_2$Cl$_2$, 10-15 min, 5-10% (1N NH$_3$/MeOH)/CH$_2$Cl$_2$, 15-20 minutes) to give 21 mg clean product (75% yield).

1H NMR (CDCl$_3$): 8.93 (s, 1H); 8.03 (dd, 1H, J=6 Hz, 20 Hz); 7.26 (m, 5H); 6.1 (br s, 1H); 5.8 (br s, 1H); 4.19 (s, 2H); 3.75 (s, 2H); 2.62 (t, 2H, J=19 Hz); 1.60 (m, 1H); 1.40 (m, 2H); 0.90 (m, 6H). MS: 312 (M+1).

We claim:
1. A compound selected from the group consisting of:
N-{4-[4-(2-Benzylamino-ethyl)-phenoxy]-phenyl}-acetamide,
N-{4-[4-(2-Hexylamino-ethyl)-phenoxy]-phenyl}-acetamide,

N-[4-(4-{2-[(Thiophen-2-ylmethyl)-amino]-ethyl}-phenoxy)-phenyl]-acetamide,
N-(4-{4-[2-(3-Phenyl-propylamino)-ethyl]-phenoxy}-phenyl)-acetamide,
N-(4-{4-[2-(2-Cyclohexyl-ethylamino)-ethyl]-phenoxy}-phenyl)-acetamide,
N-{4-[4-(2-Phenethylamino-ethyl)-phenoxy]-phenyl}-acetamide,
N-{4-[4-(2-Propylamino-ethyl)-phenoxy]-phenyl}-acetamide,
N-{4-[4-(2-Pentylamino-ethyl)-phenoxy]-phenyl}-acetamide,
N-(4-{4-[2-(Cyclohexylmethyl-amino)-ethyl]-phenoxy}-phenyl)-acetamide,
N-(4-{4-[2-(2-Trifluoromethyl-benzylamino)-ethyl]-phenoxy}-phenyl)-acetamide,
N-[4-(4-{2-[(Furan-2-ylmethyl)-amino]-ethyl}-phenoxy)-phenyl]-acetamide,
N-(4-{4-[2-(3-Chloro-benzylamino)-ethyl]-phenoxy}-phenyl)-acetamide,
N-{4-[4-(2-Benzylamino-ethyl)-phenoxy]-phenyl}-benzamide,
Morpholine-4-carboxylic acid {4-[4-(2-benzylamino-ethyl)-phenoxy]-phenyl}-amide,
N-{4-[4-(2-Benzylamino-ethyl)-phenoxy]-phenyl}-2-methoxy-acetamide,
Furan-2-carboxylic acid {4-[4-(2-benzylamino-ethyl)-phenoxy]-phenyl}-amide,
Isoxazole-5-carboxylic acid {4-[4-(2-benzylamino-ethyl)-phenoxy]-phenyl}-amide,
Thiophene-2-carboxylic acid {4-[4-(2-benzylamino-ethyl)-phenoxy]-phenyl}-amide,
N-{4-[4-(2-Benzylamino-ethyl)-phenoxy]-phenyl}-isonicotinamide,
3,5-Dimethyl-isoxazole-4-carboxylic acid {4-[4-(2-benzylamino-ethyl)-phenoxy]-phenyl}-amide,
2-tert-Butyl-5-methyl-2H-pyrazole-3-carboxylic acid {4-[4-(2-benzylamino-ethyl)-phenoxy]-phenyl}-amide,
5-Methyl-isoxazole-3-carboxylic acid {4-[4-(2-benzylamino-ethyl)-phenoxy]-phenyl}-amide,
4-Methyl-[1,2,3]thiadiazole-5-carboxylic acid {4-[4-(2-benzylamino-ethyl)-phenoxy]-phenyl}-amide,
N-{4-[4-(2-Benzylamino-ethyl)-phenoxy]-phenyl}-3-methylsulfanyl-propionamide,
Quinoxaline-2-carboxylic acid {4-[4-(2-benzylamino-ethyl)-phenoxy]-phenyl}-amide,
N-{4-[4-(2-Benzylamino-ethyl)-phenoxy]-phenyl}-nicotinamide, and
Pyridine-2-carboxylic acid {4-[4-(2-benzylamino-ethyl)-phenoxy]-phenyl}-amide,
or a pharmaceutically acceptable salt thereof.

2. A pharmaceutical composition comprising a compound according to claim 1 and a carrier, diluent and/or excipient.

3. A compound selected from the group consisting of:
{2-[4-(4-Acetylamino-phenoxy)-phenyl]-ethyl}-carbamic acid tert-butyl ester,
N-{4-[4-(2-Amino-ethyl)-phenoxy]-phenyl}-acetamide,
N-{4-[4-(2-Isobutylamino-ethyl)-phenoxy]-phenyl}-acetamide,
N-{4-[4-(2-Cyclohexylamino-ethyl)-phenoxy]-phenyl}-acetamide,
N-(4-{4-[2-(2-Methyl-benzylamino)-ethyl]-phenoxy}-phenyl)-acetamide,
N-(4-{4-[2-(3-Fluoro-benzylamino)-ethyl]-phenoxy}-phenyl)-acetamide,
N-[4-(4-{2-[(3-Methyl-thiophen-2-ylmethyl)-amino]-ethyl}-phenoxy)-phenyl]-acetamide,
N-(4-{4-[2-(3-Methyl-butylamino)-ethyl]-phenoxy}-phenyl)-acetamide,
N-(4-{4-[2-(3,5-Difluoro-benzylamino)-ethyl]-phenoxy}-phenyl)-acetamide, and
N-[4-(4-{2-[(Pyridin-3-ylmethyl)-amino]-ethyl}-phenoxy)-phenyl]-acetamide,
or a pharmaceutically acceptable salt thereof.

4. A pharmaceutical composition comprising a compound and according to claim 3 in a carrier, diluent and/or excipient.

* * * * *

UNITED STATES PATENT AND TRADEMARK OFFICE
CERTIFICATE OF CORRECTION

PATENT NO. : 7,378,448 B2  Page 1 of 1
APPLICATION NO. : 10/597127
DATED : May 27, 2008
INVENTOR(S) : Charles Howard Mitch et al.

It is certified that error appears in the above-identified patent and that said Letters Patent is hereby corrected as shown below:

On the Title page:
Insert Item --(60) Related U.S. Application Data
Provisional application no. 60/553,175, filed March 15, 2004--

Col. 1 lines 3-4 insert the following cross-reference after the title:
--This application is the national phase application, under 35
USC 371, for PCT/US2005/006723, filed March 2, 2005, which claims
the benefit, under 35 USC 119(e) of US provisional application
60/553,175 filed March 15, 2004.--

Signed and Sealed this

Thirtieth Day of November, 2010

David J. Kappos
*Director of the United States Patent and Trademark Office*